US007718598B1

(12) United States Patent
Smythe et al.

(10) Patent No.: US 7,718,598 B1
(45) Date of Patent: *May 18, 2010

(54) AUXILIARY FOR AMIDE BOND FORMATION

(75) Inventors: Mark Leslie Smythe, Queensland (AU); Wim Denis Frans Meutermans, Queensland (AU)

(73) Assignee: The University of Queensland, Brisbane, Queensland (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/787,840

(22) PCT Filed: Sep. 24, 1999

(86) PCT No.: PCT/AU99/00812

§ 371 (c)(1),
(2), (4) Date: Jul. 6, 2001

(87) PCT Pub. No.: WO00/18789

PCT Pub. Date: Apr. 6, 2000

(30) Foreign Application Priority Data

Sep. 25, 1998 (AU) .................................... PP 6165

(51) Int. Cl.
*C07K 7/00* (2006.01)
*C07K 14/00* (2006.01)

(52) U.S. Cl. ............................ 514/2; 514/10; 514/11; 514/12; 514/14; 514/9; 530/300; 530/317; 530/327; 530/330; 530/333; 530/338; 530/344

(58) Field of Classification Search .................... 514/11, 514/10, 2, 14, 9, 12; 530/317, 300, 333, 530/338, 344, 327, 330
See application file for complete search history.

(56) References Cited

U.S. PATENT DOCUMENTS

| 3,704,246 | A |   | 11/1972 | Bodanszky  | 260/333 |
|---|---|---|---|---|---|
| 5,173,499 | A | * | 12/1992 | Sindelar et al. | 514/462 |
| 5,539,138 | A |   | 7/1996 | Flanagan et al. | 558/17 |
| 5,739,386 | A |   | 4/1998 | Holmes | 562/437 |

FOREIGN PATENT DOCUMENTS

| CA | 2154214 | 1/1996 |
|---|---|---|
| EP | 0 091 330 | 10/1983 |
| WO | WO 98/17628 | 4/1998 |
| WO | WO 99/26902 | 6/1999 |
| WO | WO 00/18790 | 4/2000 |

OTHER PUBLICATIONS

Dolbeare and Vanderlaan, "A fluorescent assay of proteinases in cultured mammalian cells," *J. Histochem Cytochem.*, 27(11):1493-1495, 1979.
Francis and Jacobsen, "Discovery of novel catalysts for alkene epoxidation from metal-binding combinatorial libraries," *Agnew. Chem. Int. Ed.*, 38(7):937-941, 1999.
Janda et al., "Chemical selection for catalysis in combinatorial antibody libraries," *Science*, 275:945-948, 1997.
Kemp et al., "Peptide Synthesis with benzisoxazolium salts-I," *Tetrahedron.*, 30:3677-3688. 1974.
Murray et al., "γ-glutamyl transpeptidase demonstrated in tissue sections embedded in glycol methacrylate resin," *Histochem. J.*, 19:476-482, 1987.
International Search Report for PCT/AU99/00812, mailed Nov. 5, 1999.
Hyde et al., "Some 'Difficult Sequences' Made Easy: A Study of Interchain Association in Solid-Phase Peptide Synthesis," *Int. J. Peptide Protein Res.*, 43(5):431-440, 1994.
Johnson et al., "N,O-bisFmoc Derivatives of N-(2-Hydroxy-4-Methoxybenzyl)-Amino Acids: Useful Intermediates in Peptide Synthesis," *J. Peptide Sci.*, 1:11-25, 1995.
Kemp et al., "Intramolecular O,N-Acyl Transfer via Cyclic Intermediates of Nine and Twelve Members. Models for Extension of the Amine Capture Strategy for Peptide Synthesis," *J. Org. Chem.*, 46:490-498, 1981.
Pashayan et al., "Photorearrangement of Ortho-Nitrobenzaldehyde and its Derivatives," Translated from *Kimiya Vysokikh Energii*, 10(2):155-160, Mar.-Apr. 1976. Original article submitted Mar. 3, 1975.
Partial Supplementary European Search Report for European Counterpart Application No. 99950390.7, mailed Sep. 12, 2002.
Canne et al., "Extending the Applicability of Native Chemical Ligation," *J. Am. Chem. Soc.*, 118:5891-5896, 1996.
Cavelier-Frontin et al., "How to Perform Small Peptide Cyclizations," *J. Mol. Sruct.*, 286:125-130, 1993.
Ehrlich et al., "Cyclization of *all*-L-Pentapeptides by Means of 1-Hydroxy-7-Azabenzotriazole-Derived Uronium and Phosphonium Reagents," *J. Org. Chem.*, 61:8831-8838, 1996.

(Continued)

*Primary Examiner*—Chih-Min Kam
(74) *Attorney, Agent, or Firm*—Haynes and Boone, LLP

(57) ABSTRACT

This invention relates to methods for preparing cyclic peptides and peptidomimetic compounds in solution and bound to solid supports, and to cyclic peptide or peptidomimetic libraries for use in drug screening programmes. In particular, the invention relates to a generic strategy for synthesis of cyclic peptides or peptidomimetics that enables the efficient synthesis under mild conditions of a wide variety of desired compounds. Two approaches were evaluated for their improvements in solution and solid phase synthesis of small cyclic peptides: positioning reversible N-amide substituents in the sequence; and applying native ligation chemistry in an intramolecular sense. Systematic investigation of the effects of preorganizing peptides prior to cyclisation by using peptide cyclisation auxiliaries, and developing new linkers and peptide cyclisation auxiliaries to aid cyclic peptide synthesis gives surprising improvements in both yields and purity of products compared to the prior art methods. The combination of these technologies provides a powerful generic approach for the solution and solid phase synthesis of small cyclic peptides. The ring contraction and N-amide substitution technology of the invention provide improved methods for the synthesis of cyclic peptides and peptidomimetics. When used in conjunction with linker strategies, this combination provides solid-phase avenues to cyclic peptides and peptidomimetics.

33 Claims, 2 Drawing Sheets

OTHER PUBLICATIONS

Jensen et al., "Backbone Amide Linker (BAL) Strategy for Solid-Phase Synthesis of C-Terminal-Modified and Cyclic Peptides," *J. Am. Chem. Soc.*, 120:5441-5452, 1998.

Johnson and Quibell, "The N-(2-Hydroxybenzyl) Protecting Group for Amide Bond Protection in Solid Phase Peptide Synthesis," *Tethredron Letters*, 35(3):463-466, 1994.

Meutermans et al., "Synthesis of Difficult Cyclic Peptides by Inclusion of a Novel Photolabile Auxiliary in a Ring Contraction Strategy," *J. Am. Shem. Soc.*, 121:9790-9796, 1999.

Shao et al., "A New Method to Synthesize Cyclic Peptides," *Tethredron Letters*, 39:3911-3914, 1998.

Supplementary European Search Report for European Counterpart Application No. 99950390.7, mailed Sep. 10, 2004.

Beusen et al., "Conformational Mimicry: Synthesis and Solution Conformation of a Cyclic Somatostatin Hexapeptide Containing a Tetrazole cis Amide Bond Surrogate," *Biopolymers*, 36(2):181-260, 1995.

Botti et al., "Cyclic Peptides from Linear Unprotected Peptide Precursors Through Thiazolidine Formation," *J. Am. Chem. Soc.*, 118(42):10018-10024, 1996.

Elseviers et al., "Evidence for the Bioactive Conformation in a Cyclic Hexapeptide Analogue of Somatostatin Containing a cis Peptide Bond Mimic," *Biochem. Biophys. Res. Comm.*, 154(2):515-521, 1988.

Ruckle et al., "Pseudo-Prolines in Cyclic Peptides: Conformational Stabilisation of cyclo[Pro-Thr($\psi^{Me,\ Me}$pro)-Pro]," *Tetrahedron*, 55(37):11281-11288, 1999.

Sakurada et al., "Antinociceptive Mechanisms of [D-Arg$^2$]-Dermorphin Tripeptide Analogs," *J. Pharmacol. Exp. Therap.*, 263(2):793-799, 1992.

Salvadori et al, "Synthesis and Pharmacological Activity of Dermorphin and Its N-Terminal Sequences," *Int. J. Peptide Protein Res.*, 19(5):536-542. 1982.

Zhang and Tam, "Lactone and Lactam Library Synthesis by Silver Ion-Assisted Orthogonal Cyclization of Unprotected Peptides," *J. Am. Chem. Soc.*, 121:3311-3320, 1999.

Zhang and Tam, "Synthesis and Application of Unprotected Cyclic Peptides as Building Blocks for Peptide Dendrimers," *J. Am. Chem. Soc.*, 119:2363-2370, 1997.

Partial European Search Report for European Counterpart Application No. 99948610.3, mailed Jul. 16, 2004.

Partial Supplementary European Search Report for European Counterpart Application No. 99948610.3, mailed Sep. 12, 2002.

Abstract; Molecular Modeling of Proteins & Nucleic Acids, Dept. of Biochemistry, Virginia Tech, QSAR and Drug Design, Retrieved from /www.biochem.vt.edu/modeling/qsar_drug.html on Jun. 28, 2006.pp. 1-12.

\* cited by examiner

SEQUENCE LISTING

```
<160> NUMBER OF SEQ ID NOS: 43

<210> SEQ ID NO 1
<211> LENGTH: 4
<212> TYPE: PRT
<213> ORGANISM: ARTIFICIAL
<220> FEATURE:
<223> OTHER INFORMATION: SYNTHETIC LINEAR PEPTIDE
<220> FEATURE:
<221> NAME/KEY: MISC_FEATURE
<222> LOCATION: (1)..(1)
<223> OTHER INFORMATION: Xaa = HS-(CH2)2-Tyr
<220> FEATURE:
<221> NAME/KEY: MISC_FEATURE
<222> LOCATION: (4)..(4)
<223> OTHER INFORMATION: Xaa = Gly-OH

<400> SEQUENCE: 1

Xaa Arg Phe Xaa
1

<210> SEQ ID NO 2
<211> LENGTH: 4
<212> TYPE: PRT
<213> ORGANISM: ARTIFICIAL
<220> FEATURE:
<223> OTHER INFORMATION: SYNTHETIC LINEAR PEPTIDE
<220> FEATURE:
<221> NAME/KEY: MISC_FEATURE
<222> LOCATION: (1)..(1)
<223> OTHER INFORMATION: Xaa = butyl-Tyr substituted
<220> FEATURE:
<221> NAME/KEY: MISC_FEATURE
<222> LOCATION: (2)..(2)
```

```
<223> OTHER INFORMATION: Xaa = 2,2,5,7,8-pentamethylchroman-6-sulfonyl-Arg
<220> FEATURE:
<221> NAME/KEY: MISC_FEATURE
<222> LOCATION: (4)..(4)
<223> OTHER INFORMATION: Xaa = Gly WANG resin

<400> SEQUENCE: 2

Xaa Xaa Phe Xaa
1

<210> SEQ ID NO 3
<211> LENGTH: 4
<212> TYPE: PRT
<213> ORGANISM: ARTIFICIAL
<220> FEATURE:
<223> OTHER INFORMATION: SYNTHETIC LINEAR PEPTIDE
<220> FEATURE:
<221> NAME/KEY: MISC_FEATURE
<222> LOCATION: (1)..(1)
<223> OTHER INFORMATION: Xaa = N-(5-nitro-2-mercaptobenzyl)-Tyr
<220> FEATURE:
<221> NAME/KEY: MISC_FEATURE
<222> LOCATION: (4)..(4)
<223> OTHER INFORMATION: Xaa = Gly-OH

<400> SEQUENCE: 3

Xaa Arg Phe Xaa
1

<210> SEQ ID NO 4
<211> LENGTH: 5
<212> TYPE: PRT
<213> ORGANISM: ARTIFICIAL
<220> FEATURE:
<223> OTHER INFORMATION: SYNTHETIC LINEAR PEPTIDE
<220> FEATURE:
<221> NAME/KEY: MISC_FEATURE
<222> LOCATION: (1)..(1)
<223> OTHER INFORMATION: Xaa = HS-(CH2)2-Ala
<220> FEATURE:
<221> NAME/KEY: MISC_FEATURE
<222> LOCATION: (5)..(5)
<223> OTHER INFORMATION: Xaa = Ala-OH

<400> SEQUENCE: 4

Xaa Phe Leu Pro Xaa
1               5

<210> SEQ ID NO 5
<211> LENGTH: 5
<212> TYPE: PRT
<213> ORGANISM: ARTIFICIAL
<220> FEATURE:
<223> OTHER INFORMATION: SYNTHETIC LINEAR PEPTIDE
<220> FEATURE:
<221> NAME/KEY: MISC_FEATURE
<222> LOCATION: (5)..(5)
<223> OTHER INFORMATION: Xaa = Ala-WANG resin

<400> SEQUENCE: 5

Ala Phe Leu Pro Xaa
1               5

<210> SEQ ID NO 6
<211> LENGTH: 4
<212> TYPE: PRT
<213> ORGANISM: ARTIFICIAL
<220> FEATURE:
<223> OTHER INFORMATION: SYNTHETIC LINEAR PEPTIDE
<220> FEATURE:
<221> NAME/KEY: MISC_FEATURE
```

```
<222> LOCATION: (1)..(1)
<223> OTHER INFORMATION: Xaa = HS-(CH2)2-NH-CH(CH3)-CO-Phe
<220> FEATURE:
<221> NAME/KEY: MISC_FEATURE
<222> LOCATION: (4)..(4)
<223> OTHER INFORMATION: Xaa = Ala-OH

<400> SEQUENCE: 6

Xaa Leu Pro Xaa
1

<210> SEQ ID NO 7
<211> LENGTH: 5
<212> TYPE: PRT
<213> ORGANISM: ARTIFICIAL
<220> FEATURE:
<223> OTHER INFORMATION: SYNTHETIC LINEAR PEPTIDE
<220> FEATURE:
<221> NAME/KEY: MISC_FEATURE
<222> LOCATION: (1)..(1)
<223> OTHER INFORMATION: Xaa = N-(2-hydroxy-5-nitrobenzyl)-Ala
<220> FEATURE:
<221> NAME/KEY: MISC_FEATURE
<222> LOCATION: (5)..(5)
<223> OTHER INFORMATION: Xaa = Ala-OH

<400> SEQUENCE: 7

Xaa Phe Leu Pro Xaa
1               5

<210> SEQ ID NO 8
<211> LENGTH: 5
<212> TYPE: PRT
<213> ORGANISM: ARTIFICIAL
<220> FEATURE:
<223> OTHER INFORMATION: SYNTHETIC LINEAR PEPTIDE
<220> FEATURE:
<221> NAME/KEY: MISC_FEATURE
<222> LOCATION: (1)..(1)
<223> OTHER INFORMATION: Xaa a= N-(2-hydroxy-6-nitrobenzyl)-Ala
<220> FEATURE:
<221> NAME/KEY: MISC_FEATURE
<222> LOCATION: (5)..(5)
<223> OTHER INFORMATION: Xaa = Ala-OH

<400> SEQUENCE: 8

Xaa Phe Leu Pro Xaa
1               5

<210> SEQ ID NO 9
<211> LENGTH: 4
<212> TYPE: PRT
<213> ORGANISM: ARTIFICIAL
<220> FEATURE:
<223> OTHER INFORMATION: SYNTHETIC LINEAR PEPTIDE

<400> SEQUENCE: 9

Val Ala Gly Phe
1

<210> SEQ ID NO 10
<211> LENGTH: 5
<212> TYPE: PRT
<213> ORGANISM: ARTIFICIAL
<220> FEATURE:
<223> OTHER INFORMATION: SYNTHETIC CYCLIC PEPTIDE

<400> SEQUENCE: 10

Ala Phe Leu Pro Ala
1               5
```

```
<210> SEQ ID NO 11
<211> LENGTH: 5
<212> TYPE: PRT
<213> ORGANISM: ARTIFICIAL
<220> FEATURE:
<223> OTHER INFORMATION: SYNTHETIC LINEAR PEPTIDE
<220> FEATURE:
<221> NAME/KEY: MISC_FEATURE
<222> LOCATION: (1)..(1)
<223> OTHER INFORMATION: Xaa = N-(6-nitro-2-hydroxybenzyl)-Phe

<400> SEQUENCE: 11

Xaa Leu Pro Ala Ala
1               5

<210> SEQ ID NO 12
<211> LENGTH: 5
<212> TYPE: PRT
<213> ORGANISM: ARTIFICIAL
<220> FEATURE:
<223> OTHER INFORMATION: SYNTHETIC CYCLIC PEPTIDE
<220> FEATURE:
<221> NAME/KEY: MISC_FEATURE
<222> LOCATION: (1)..(1)
<223> OTHER INFORMATION: Xaa = S-(CH2)2-Ala

<400> SEQUENCE: 12

Xaa Phe Leu Pro Ala
1               5

<210> SEQ ID NO 13
<211> LENGTH: 5
<212> TYPE: PRT
<213> ORGANISM: ARTIFICIAL
<220> FEATURE:
<223> OTHER INFORMATION: SYNTHETIC LINEAR PEPTIDE
<220> FEATURE:
<221> NAME/KEY: MISC_FEATURE
<222> LOCATION: (1)..(1)
<223> OTHER INFORMATION: Xaa = HS-(CH2)2-Ala

<400> SEQUENCE: 13

Xaa Phe Leu Pro Ala
1               5

<210> SEQ ID NO 14
<211> LENGTH: 8
<212> TYPE: PRT
<213> ORGANISM: ARTIFICIAL
<220> FEATURE:
<223> OTHER INFORMATION: SYNTHETIC CYCLIC PEPTIDE
<220> FEATURE:
<221> NAME/KEY: MISC_FEATURE
<222> LOCATION: (1)..(1)
<223> OTHER INFORMATION: Xaa = S-(CH2)2-NH-CH(CH3)-CO-Phe
<220> FEATURE:
<221> NAME/KEY: MISC_FEATURE
<222> LOCATION: (4)..(4)
<223> OTHER INFORMATION: Xaa = Ala-NH2
<220> FEATURE:
<221> NAME/KEY: MISC_FEATURE
<222> LOCATION: (5)..(5)
<223> OTHER INFORMATION: Xaa = S-(CH2)2-NH-CH(CH3)-CO-Phe
<220> FEATURE:
<221> NAME/KEY: MISC_FEATURE
<222> LOCATION: (8)..(8)
<223> OTHER INFORMATION: Xaa = Ala-OH

<400> SEQUENCE: 14

Xaa Leu Pro Xaa Xaa Leu Pro Xaa
```

-continued

```
1               5

<210> SEQ ID NO 15
<211> LENGTH: 5
<212> TYPE: PRT
<213> ORGANISM: ARTIFICIAL
<220> FEATURE:
<223> OTHER INFORMATION: SYNTHETIC LINEAR PEPTIDE
<220> FEATURE:
<221> NAME/KEY: MISC_FEATURE
<222> LOCATION: (1)..(1)
<223> OTHER INFORMATION: Xaa = N-(5-nitro-2-hydroxybenzyl)-Ala

<400> SEQUENCE: 15

Xaa Phe Leu Pro Ala
1               5

<210> SEQ ID NO 16
<211> LENGTH: 5
<212> TYPE: PRT
<213> ORGANISM: ARTIFICIAL
<220> FEATURE:
<223> OTHER INFORMATION: SYNTHETIC CYCLIC PEPTIDE
<220> FEATURE:
<221> NAME/KEY: MISC_FEATURE
<222> LOCATION: (1)..(1)
<223> OTHER INFORMATION: Xaa = N-(6-nitro-2-hydroxybenzyl)-Ala

<400> SEQUENCE: 16

Xaa Phe Leu Pro Ala
1               5

<210> SEQ ID NO 17
<211> LENGTH: 5
<212> TYPE: PRT
<213> ORGANISM: ARTIFICIAL
<220> FEATURE:
<223> OTHER INFORMATION: SYNTHETIC CYCLIC PEPTIDE
<220> FEATURE:
<221> NAME/KEY: MISC_FEATURE
<222> LOCATION: (1)..(1)
<223> OTHER INFORMATION: Xaa = N-(6-nitro-2-hydroxybenzyl)-Phe

<400> SEQUENCE: 17

Xaa Leu Pro Ala Ala
1               5

<210> SEQ ID NO 18
<211> LENGTH: 5
<212> TYPE: PRT
<213> ORGANISM: ARTIFICIAL
<220> FEATURE:
<223> OTHER INFORMATION: SYNTHETIC LINEAR PEPTIDE
<220> FEATURE:
<221> NAME/KEY: MISC_FEATURE
<222> LOCATION: (1)..(1)
<223> OTHER INFORMATION: Xaa = N-(6-nitro-2-hydroxybenzyl)-Phe

<400> SEQUENCE: 18

Xaa Leu Pro Ala Ala
1               5

<210> SEQ ID NO 19
<211> LENGTH: 5
<212> TYPE: PRT
<213> ORGANISM: ARTIFICIAL
<220> FEATURE:
<223> OTHER INFORMATION: SYNTHETIC LINEAR PEPTIDE

<400> SEQUENCE: 19
```

Ala Phe Leu Pro Ala
1               5

<210> SEQ ID NO 20
<211> LENGTH: 5
<212> TYPE: PRT
<213> ORGANISM: ARTIFICIAL
<220> FEATURE:
<223> OTHER INFORMATION: SYNTHETIC CYCLIC PEPTIDE

<400> SEQUENCE: 20

Phe Leu Pro Ala Ala
1               5

<210> SEQ ID NO 21
<211> LENGTH: 4
<212> TYPE: PRT
<213> ORGANISM: ARTIFICIAL
<220> FEATURE:
<223> OTHER INFORMATION: SYNTHETIC LINEAR PEPTIDE

<400> SEQUENCE: 21

Tyr Arg Phe Gly
1

<210> SEQ ID NO 22
<211> LENGTH: 4
<212> TYPE: PRT
<213> ORGANISM: ARTIFICIAL
<220> FEATURE:
<223> OTHER INFORMATION: SYNTHETIC LINEAR PEPTIDE
<220> FEATURE:
<221> NAME/KEY: MISC_FEATURE
<222> LOCATION: (1)..(1)
<223> OTHER INFORMATION: Xaa = N-(2-hydroxy-6-nitrobenzyl) substituted
      Tyr

<400> SEQUENCE: 22

Xaa Arg Phe Gly
1

<210> SEQ ID NO 23
<211> LENGTH: 4
<212> TYPE: PRT
<213> ORGANISM: ARTIFICIAL
<220> FEATURE:
<223> OTHER INFORMATION: SYNTHETIC CYCLIC PEPTIDE
<220> FEATURE:
<221> NAME/KEY: MISC_FEATURE
<222> LOCATION: (1)..(1)
<223> OTHER INFORMATION: Xaa = N-(2-hydroxy-6-nitrobenzyl) substituted
      Tyr

<400> SEQUENCE: 23

Xaa Arg Phe Gly
1

<210> SEQ ID NO 24
<211> LENGTH: 4
<212> TYPE: PRT
<213> ORGANISM: ARTIFICIAL
<220> FEATURE:
<223> OTHER INFORMATION: SYNTHETIC CYCLIC PEPTIDE

<400> SEQUENCE: 24

Tyr Arg Phe Gly
1

```
<210> SEQ ID NO 25
<211> LENGTH: 5
<212> TYPE: PRT
<213> ORGANISM: ARTIFICIAL
<220> FEATURE:
<223> OTHER INFORMATION: SYNTHETIC LINEAR PEPTIDE

<400> SEQUENCE: 25

Leu Tyr Arg Ala Gly
1               5

<210> SEQ ID NO 26
<211> LENGTH: 5
<212> TYPE: PRT
<213> ORGANISM: ARTIFICIAL
<220> FEATURE:
<223> OTHER INFORMATION: SYNTHETIC LINEAR PEPTIDE

<400> SEQUENCE: 26

Gly Ala Gly Pro Ala
1               5

<210> SEQ ID NO 27
<211> LENGTH: 10
<212> TYPE: PRT
<213> ORGANISM: ARTIFICIAL
<220> FEATURE:
<223> OTHER INFORMATION: SYNTHETIC LINEAR PEPTIDE

<400> SEQUENCE: 27

Leu Tyr Arg Ala Gly Gly Ala Gly Pro Ala
1               5                   10

<210> SEQ ID NO 28
<211> LENGTH: 5
<212> TYPE: PRT
<213> ORGANISM: ARTIFICIAL
<220> FEATURE:
<223> OTHER INFORMATION: SYNTHETIC LINEAR PEPTIDE

<400> SEQUENCE: 28

Leu Tyr Arg Ala Phe
1               5

<210> SEQ ID NO 29
<211> LENGTH: 5
<212> TYPE: PRT
<213> ORGANISM: ARTIFICIAL
<220> FEATURE:
<223> OTHER INFORMATION: SYNTHETIC LINEAR PEPTIDE

<400> SEQUENCE: 29

Ala Ala Arg His Thr
1               5

<210> SEQ ID NO 30
<211> LENGTH: 10
<212> TYPE: PRT
<213> ORGANISM: ARTIFICIAL
<220> FEATURE:
<223> OTHER INFORMATION: SYNTHETIC LINEAR PEPTIDE

<400> SEQUENCE: 30

Leu Tyr Arg Ala Phe Ala Ala Arg His Thr
1               5                   10
```

```
<210> SEQ ID NO 31
<211> LENGTH: 5
<212> TYPE: PRT
<213> ORGANISM: ARTIFICIAL
<220> FEATURE:
<223> OTHER INFORMATION: SYNTHETIC LINEAR PEPTIDE

<400> SEQUENCE: 31

Phe Leu Pro Ala Ala
1               5

<210> SEQ ID NO 32
<211> LENGTH: 4
<212> TYPE: PRT
<213> ORGANISM: ARTIFICIAL
<220> FEATURE:
<223> OTHER INFORMATION: SYNTHETIC CYCLIC PEPTIDE

<400> SEQUENCE: 32

Phe Phe Phe Phe
1

<210> SEQ ID NO 33
<211> LENGTH: 14
<212> TYPE: PRT
<213> ORGANISM: ARTIFICIAL
<220> FEATURE:
<223> OTHER INFORMATION: SYNTHETIC LINEAR PEPTIDE

<400> SEQUENCE: 33

Tyr Ala Val Thr Gly Arg Gly Asp Ser Pro Ala Ala Ser Ser
1               5                   10

<210> SEQ ID NO 34
<211> LENGTH: 16
<212> TYPE: PRT
<213> ORGANISM: ARTIFICIAL
<220> FEATURE:
<223> OTHER INFORMATION: SYNTHETIC CYCLIC PEPTIDE

<400> SEQUENCE: 34

Cys Tyr Ala Val Thr Gly Arg Gly Asp Ser Pro Ala Ala Ser Ser Gly
1               5                   10                  15

<210> SEQ ID NO 35
<211> LENGTH: 11
<212> TYPE: PRT
<213> ORGANISM: ARTIFICIAL
<220> FEATURE:
<223> OTHER INFORMATION: SYNTHETIC LINEAR PEPTIDE

<400> SEQUENCE: 35

Val Ser Ile Leu Glu Thr Lys Ile Tyr Gly Thr
1               5                   10

<210> SEQ ID NO 36
<211> LENGTH: 5
<212> TYPE: PRT
<213> ORGANISM: ARTIFICIAL
<220> FEATURE:
<223> OTHER INFORMATION: SYNTHETIC LINEAR PEPTIDE
<220> FEATURE:
<221> NAME/KEY: MISC_FEATURE
<222> LOCATION: (5)..(5)
<223> OTHER INFORMATION: Xaa = Ala-Trityl resin

<400> SEQUENCE: 36

Ala Phe Leu Pro Xaa
```

```
1               5

<210> SEQ ID NO 37
<211> LENGTH: 4
<212> TYPE: PRT
<213> ORGANISM: ARTIFICIAL
<220> FEATURE:
<223> OTHER INFORMATION: SYNTHETIC LINEAR PEPTIDE
<220> FEATURE:
<221> NAME/KEY: MISC_FEATURE
<222> LOCATION: (4)..(4)
<223> OTHER INFORMATION: Xaa = Phe-resin

<400> SEQUENCE: 37

Val Ala Gly Xaa
1

<210> SEQ ID NO 38
<211> LENGTH: 11
<212> TYPE: PRT
<213> ORGANISM: ARTIFICIAL
<220> FEATURE:
<223> OTHER INFORMATION: SYNTHETIC LINEAR PEPTIDE

<400> SEQUENCE: 38

Thr Gly Tyr Ile Lys Thr Glu Leu Ile Ser Val
1               5                   10

<210> SEQ ID NO 39
<211> LENGTH: 5
<212> TYPE: PRT
<213> ORGANISM: ARTIFICIAL
<220> FEATURE:
<223> OTHER INFORMATION: SYNTHETIC LINEAR PEPTIDE
<220> FEATURE:
<221> NAME/KEY: MISC_FEATURE
<222> LOCATION: (1)..(1)
<223> OTHER INFORMATION: Xaa = H-Ala
<220> FEATURE:
<221> NAME/KEY: MISC_FEATURE
<222> LOCATION: (5)..(5)
<223> OTHER INFORMATION: Xaa = Ala-OH

<400> SEQUENCE: 39

Xaa Phe Leu Pro Xaa
1               5

<210> SEQ ID NO 40
<211> LENGTH: 8
<212> TYPE: PRT
<213> ORGANISM: ARTIFICIAL
<220> FEATURE:
<223> OTHER INFORMATION: SYNTHETIC CYCLIC PEPTIDE
<220> FEATURE:
<221> NAME/KEY: MISC_FEATURE
<222> LOCATION: (1)..(1)
<223> OTHER INFORMATION: Xaa = S-(CH2)2-NH-CH(CH3)-CO-Phe
<220> FEATURE:
<221> NAME/KEY: MISC_FEATURE
<222> LOCATION: (4)..(4)
<223> OTHER INFORMATION: Xaa = Ala-NH2
<220> FEATURE:
<221> NAME/KEY: MISC_FEATURE
<222> LOCATION: (5)..(5)
<223> OTHER INFORMATION: Xaa = S-(CH2)2-NH-CH(CH3)-CO-Phe
<220> FEATURE:
<221> NAME/KEY: MISC_FEATURE
<222> LOCATION: (8)..(8)
<223> OTHER INFORMATION: Xaa = Ala-NH2

<400> SEQUENCE: 40
```

```
Xaa Leu Pro Xaa Xaa Leu Pro Xaa
1               5

<210> SEQ ID NO 41
<211> LENGTH: 8
<212> TYPE: PRT
<213> ORGANISM: ARTIFICIAL
<220> FEATURE:
<223> OTHER INFORMATION: SYNTHETIC LINEAR PEPTIDE
<220> FEATURE:
<221> NAME/KEY: MISC_FEATURE
<222> LOCATION: (1)..(1)
<223> OTHER INFORMATION: Xaa = S-(CH2)2-NH-CH(CH3)-CO-Phe
<220> FEATURE:
<221> NAME/KEY: MISC_FEATURE
<222> LOCATION: (4)..(4)
<223> OTHER INFORMATION: Xaa = Ala-OH
<220> FEATURE:
<221> NAME/KEY: MISC_FEATURE
<222> LOCATION: (5)..(5)
<223> OTHER INFORMATION: Xaa = S-(CH2)2-NH-CH(CH3)-CO-Phe
<220> FEATURE:
<221> NAME/KEY: MISC_FEATURE
<222> LOCATION: (8)..(8)
<223> OTHER INFORMATION: Xaa = Ala-OH

<400> SEQUENCE: 41

Xaa Leu Pro Xaa Xaa Leu Pro Xaa
1               5

<210> SEQ ID NO 42
<211> LENGTH: 5
<212> TYPE: PRT
<213> ORGANISM: ARTIFICIAL
<220> FEATURE:
<223> OTHER INFORMATION: SYNTHETIC CYCLIC PEPTIDE
<220> FEATURE:
<221> NAME/KEY: MISC_FEATURE
<222> LOCATION: (1)..(1)
<223> OTHER INFORMATION: Xaa = N-(5-nitro-2-hydroxybenzyl)-Ala

<400> SEQUENCE: 42

Xaa Phe Leu Pro Ala
1               5

<210> SEQ ID NO 43
<211> LENGTH: 5
<212> TYPE: PRT
<213> ORGANISM: ARTIFICIAL
<220> FEATURE:
<223> OTHER INFORMATION: SYNTHETIC LINEAR PEPTIDE
<220> FEATURE:
<221> NAME/KEY: MISC_FEATURE
<222> LOCATION: (1)..(1)
<223> OTHER INFORMATION: Xaa = N-(6-nitro-2-hydroxybenzyl)-Ala

<400> SEQUENCE: 43

Xaa Phe Leu Pro Ala
1               5
```

AUXILIARY FOR AMIDE BOND FORMATION

The present application is a nationalization of International Patent Application PCT/AU99/00812, filed Sep. 24, 1999, which claims priority to Australian Patent Application PP 6165, filed Sep. 25, 1998.

FIELD OF THE INVENTION

This invention relates to novel auxiliaries for the formation of amide bonds, and to the use of these auxiliaries in a variety of synthetic applications. In particular, the auxiliaries of the invention are useful in the synthesis of peptides and peptidomimetic compounds, and in particular for the synthesis of "small cyclic peptides", so-called "difficult" peptide sequences, and large peptides with a native peptide backbone. The auxiliaries of the invention are also useful in the synthesis of peptides or of C-terminal modified peptides, and in on-resin cyclisation of organic molecules, ligating chemistry, backbone substitution and as backbone linkers. In a particularly preferred embodiment, the invention provides auxiliaries that can be removed by photolysis.

BACKGROUND OF THE INVENTION

Amide bond formation is one of the most studied reactions in chemistry and biology. It allows peptide and protein synthesis, and enables the synthesis of peptide-like molecules, known as peptidomimetic compounds, which are widely used in drug design and discovery programs. A plethora of reagents and reaction conditions have been developed over the years that facilitate amide bond formation by activating a carboxylic acid and mixing it with a primary or secondary amine. In a number of cases however the acylation reaction may not go to completion or may not proceed at all. Despite the progress and extensive research efforts in this field, so-called "difficult" amide bonds still exist that prevent access to a large number of compounds of great interest to the research community. In particular these include small cyclic peptides, large peptides and proteins and difficult peptide sequences. In these cases, attempts to force the acylation by heating or by increasing the activity of the activated ester result in undesirable side reactions, such as racemisation, or dimerisation. In these cases a different approach is required to facilitate the amide bond formation. In the past 10 years a number of auxiliary strategies have been developed that make use of an intramolecular acyl transfer to overcome some of these problems. These strategies and their targets are outlined in more detail below.

1. Native Ligation Chemistry

The general idea of chemical ligation is to synthesise large proteins in high purity. The process capitalises on the ability to generate highly homogeneous linear peptides of up to 50 residues long by using optimised solid phase peptide synthesis. These peptide segments are then linked or ligated in solution, using mutually reactive entities at the end of each segment. The major limitation to the existing ligation strategies is that they only work for a very limited number of ligation sites.

Several examples have been published where mutually reactive groups generate an amide isostere. In these first examples the ligation chemistry produced a modification in the peptide backbone of the product. In 1986, Kemp et al (1986) proposed a thiol-capture strategy, which is illustrated in Scheme 1.

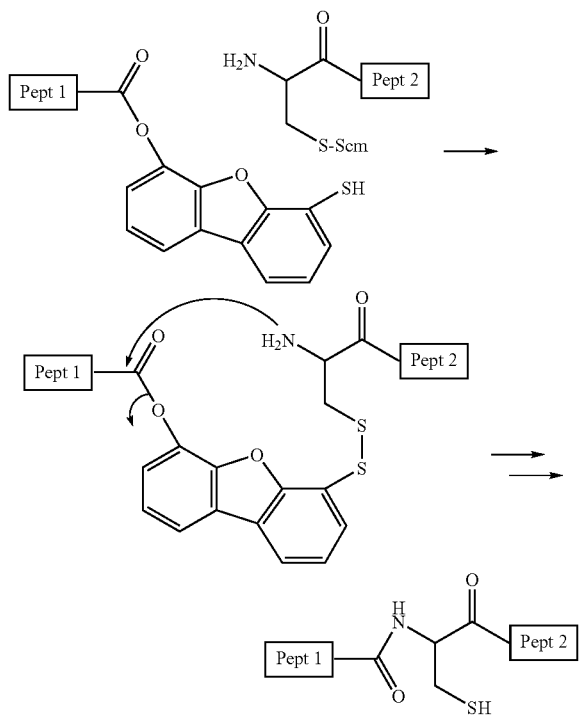

Scheme 1 The thiol-capture strategy

Here two peptide segments are ligated using a mercaptobenzofuran substituent at the C-terminus of the first segment. The second segment, carrying a cysteine residue at the N-terminus, reacts to form a disulfide link. Following an O-to-N-acyl shift the disulfide link is cleaved, generating a "native" amide bond. This auxiliary strategy, although revolutionary in its own right, lacks versatility and has only been used successfully in a very limited number of cases (Fotouhi et al, 1989) due to the inherent difficulties in synthesising the selectively-protected peptide segments. It differs from our invention in the strategic approach and the design of the auxiliary. The same group has studied a number of parameters that influence the rate of the intramolecular acyl transfer, mostly focussing on the shape of the auxiliary (Kemp et al, 1981). This work is very different from our invention, and in no way suggested anything that is described in this invention.

In 1994 Dawson et al (1994) introduced the concept of native ligation, which allows the generation of proteins with a native or unmodified backbone from fully unprotected building blocks. This approach, outlined in Scheme 2, uses chemistry first described by Wieland for reacting amino acids.

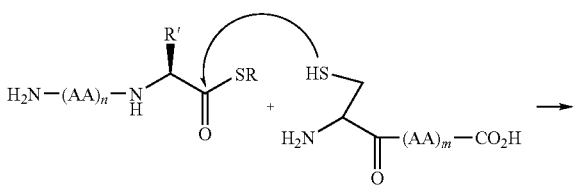

Scheme 2 "Native ligation"

-continued

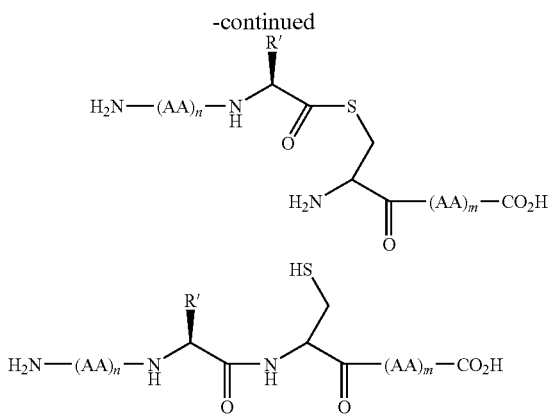

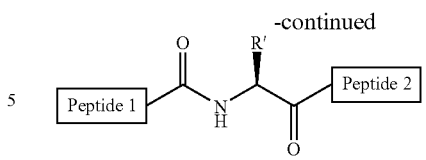

In a first step an unprotected peptide-α-thioester selectively reacts with the thiol functionality on the N-terminal cysteine side chain of a second unprotected peptide. The initially-formed thioester undergoes a spontaneous acyl transfer in the aqueous buffer from a sulfur to a nitrogen atom, thereby generating a standard peptide bond. Several examples illustrate the significance of this work in enabling the synthesis of large proteins in high purity (Hackeng et al, 1997). One of the limitations of this native ligation strategy is that it relies on the presence of a cysteine residue somewhere in the middle of the target peptide sequence.

In an extension of this work, Canne et al (1996) reported a native ligation strategy that uses an auxiliary at the N-terminus of one of the peptide segments. The strategy avoids the necessity for an N-terminal cysteine residue, and expands the range of sites amenable to native chemical ligation to X-Gly and Gly-X. The strategy is outlined in Scheme 3.

Scheme 3 Extension of native ligation

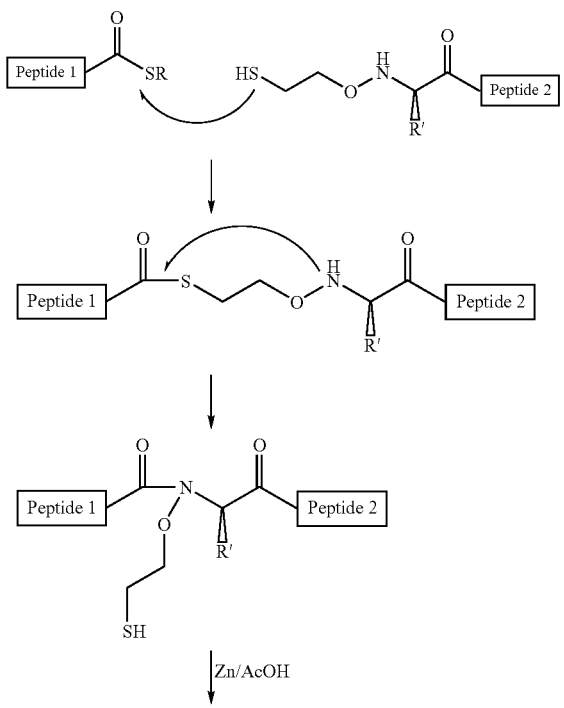

A peptide-α-thioester reacts with an $N^\alpha$ (oxyethanethiol) peptide to produce the ligated product. The thioester-linked intermediate rearranges via an acyl transfer to an amide-linked product. The N—O bond at the tertiary amide can be readily cleaved using zinc dust in acidic aqueous solution, thereby releasing the oxyethanethiol auxiliary and producing the native backbone structure in the ligated product. The scope and limitation of this auxiliary approach was examined by selecting a range of different ligation sites.

It was found that the S-to-N acyl transfer only proceeded well for Gly-Gly ligation sites, but was more difficult when steric hindrance around the ligation site was increased. For example, in the case of a Gly-Ala ligation site the rearrangement, was incomplete after 10 hours in the pH 7.5 buffer. Lowering the pH to 4.5 accelerated the rearrangement, which was complete after 10 hours. In the case of a Phe-Gly ligation site rearrangement was almost complete after 2 days at 37° C. For the more hindered Phe-Ala ligation site no S-to-N acyl transfer step was observed, even after lowering the pH or leaving the sample at 37° C. for 24 hours. It was thus concluded that only Gly-X or X-Gly ligation sites will produce the target product. The limitation lies in the acyl-transfer step, which does not proceed for hindered ligation sites. The strategy differs from our invention in the way the auxiliary is introduced and removed, and in the design of the auxiliary.

Native ligations have also been performed using resin-bound peptides. One such strategy (Camarero et al, 1998) involves the assembly of a first peptide segment linked via a C-terminal thioester to the solid support, then adding the second segment containing a cysteine residue at the N-terminus, and performing the native ligation steps as for solution phase ligation. This has the advantage that handling of the intermediates is significantly reduced. Furthermore, several ligations can be performed in series using the same chemical approach. The limitations for the solid phase approaches are the same as for the solution phase chemistry, ie native ligation can only be performed at X-Cys, Gly-X or X-Gly sites.

2. Small Cyclic Peptides

Proteins and peptides are the primary means of initiating biological processes by interacting with macromolecular receptors. The crucial information determining the specific activity is often contained in relatively small sequences at the surface, and is determined by the three-dimensional conformation in which that sequence positions its side chains when interacting with the receptor. In the linear form, bioactive peptides can assume millions of different conformations, only very few of which are able to bind to the target receptor. In order to assess the important structural and dynamic properties that are critical to the biological potency and selectivity, conformational constraints are introduced, typically through cyclisation. Such cyclic molecules exist in more defined conformations, and are therefore very appealing from the point of view of pharmaceutical lead discovery. If activity is maintained or enhanced in these cyclic peptides, structural information is obtained, for example by NMR, X-ray or molecular modelling, and used to guide the development of therapeutic drugs. In addition, cyclisation generally promotes an increase of metabolic stability and bioavailability of peptides.

As the side chains are considered the main mediators for receptor interaction, cyclisation is preferably accomplished between the C- and N-termini. Whereas the synthesis of linear peptides generally proceeds well, head-to-tail cyclisation is often troublesome. This is particularly so for small peptides, ie. those less than seven residues long. All-L cyclic tetrapeptides for instance are not very accessible (Schmidt and Langner, 1997). The primary reason for ineffective cyclisation originates from what are called "difficult sequences". In cyclisation terms this refers to a sequence-related inefficiency in "bringing the ends together" for head-to-tail cyclisation. Peptide bonds have strong π-character, and preferentially adopt a trans conformation. Linear precursors are therefore generally extended in conformation with terminal carboxylic acid and amine functional groups in remote positions, and are thus unfavourable for cyclisation. The problem is most prominent in the synthesis of small cyclic peptides, where activation of the C-terminus often results in the formation of linear and cyclic dimers or oligomers with low or no yield of target cyclic monomer.

There have been very few studies that address the "difficult" cyclisation issue. Cavalier-Frontin et al (1993) reported on the use of reversible chemical modifications of the peptide backbone to enhance cis-amide conformations. In the synthesis of cyclo-[Phe-Phe-Phe-Phe] (SEQ ID NO:32), each amide N was substituted with a BOC protecting group. The cyclisation yield increased from 1% to 27%. Similarly, the use of the N-(2-hydroxy-4-methoxybenzyl) (Hmb) group as a reversible N-backbone amide substituent has resulted in increases in yield of cyclic peptides (Ehrlich et al, 1996). It must be emphasised that here the "auxiliary" is placed on the backbone amide, and not on the N-terminal amine that reacts to form the "difficult" amide bond.

In the past two to three years a few studies where ligation chemistry was used in an intramolecular fashion have been reported. In these examples an initially larger ring is formed, and ring contraction accomplished through an intramolecular O-to-N or S-to-N acyl transfer.

In a first method reported by Botti et al (1996), linear unprotected peptides carrying a cysteine residue at the N-terminus and an aldehyde at the C-terminus, were cyclised to generate a thiazolidine containing cyclic peptide, as shown in Scheme 4. Initially a larger cycle is formed, in which the C- and N-termini are prepositioned for O-to-N acyl transfer and ring contraction to a smaller cycle. The disadvantage of this method is that the cyclic product always contains a thiazolidine moiety in the cycle, with an additional chiral centre which results in the formation of two diastereomers, and requires a cysteine residue at the N-terminus of the linear precursor. The method does not allow the generation of unmodified cyclic peptides, and is not a versatile procedure suitable for a combinatorial library approach.

Scheme 4 Ring contraction chemistry using a thiazolidine unit in the ring

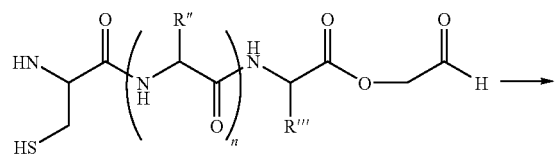

-continued

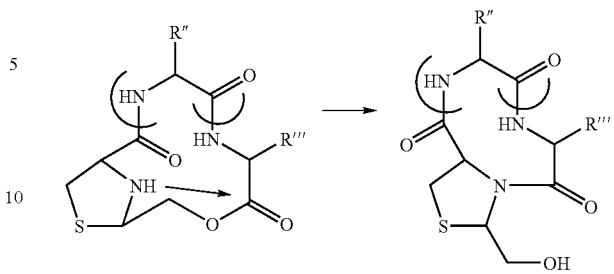

Muir et al demonstrated that "native" ligation, using a cysteine residue at the N-terminus and a thioester at the C-terminus, can be applied in an intramolecular way to generate cyclic peptides (Camarero and Muir, 1997), as shown in Scheme 5. In Scheme 5, YAVTGRGDSPAASS is SEQ ID NO:33 and cyclo-CYAVTGRGDSPAASSG is SEQ ID NO:34.

Scheme 5 Intramolecular native ligation using cysteine

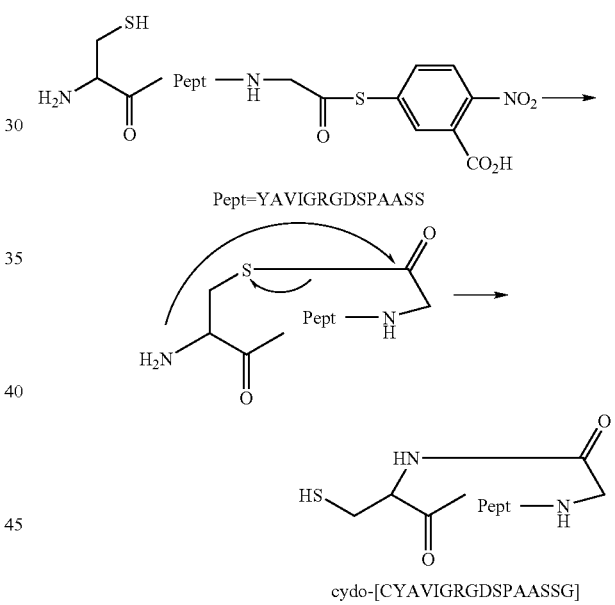

cyclo-[CYAVIGRGDSPAASSG]

A 15-residue unprotected peptide containing a C-terminal thioacid was converted to the head-to-tail cyclic peptide by dissolving the activated $C^\alpha$-thioester in a pH 7.5 buffer. Cyclisation was complete in 10 minutes. The initially formed cyclic thioester rearranges quickly to form the final peptide bond. The strategy is not generic, as it requires a cysteine residue at the N-terminus.

In a similar way Shao et al (1998) showed that N-(oxyethanethiol)-glycine at the N-terminus can be employed to achieve cyclisation by allowing the thiol functionality to react regioselectively with a thioester at the C-terminus. These strategies, as the authors point out, are limited by the types of residues involved at the C- and N-termini. Cyclisation is only possible between Gly-X, where X is a non β-substituted residue. The slow acyl transfer is again the limiting factor in this cyclisation strategy.

None of these methods provides a versatile synthetic route to enable synthesis of cyclic peptides with unmodified or native peptide backbone. The first two methods require the presence of cysteine at the N-terminus and the last lacks versatility, as the ring contraction only proceeds for non-hindered cases. We have found that the latter approach does not provide access to a number of known "difficult" cyclic peptides.

3. Backbone Substitution

One of the major problems in solid phase peptide synthesis (SPPS) is the inefficient assembly of the so-called "difficult" sequences. Moreover, these sequence-related difficulties are impossible to predict a priori. The problems are believed to be mainly due to inter- and intra-chain aggregation during the assembly of the protected peptide on the solid support. This has led to the development of the backbone substitution strategy (Hyde et al, 1994) outlined below in Scheme 6. A 2-hydroxy-4-methoxybenzyl substituent (=Hmb) is introduced by using N,O-bis-Fmoc-protected (Hmb)-amino acids. In general acylation of N-substituted amino acids other than glycine requires forcing conditions, due to the massive steric hindrance imposed by the N-substituent. In the case of the Hmb-substituted amino acids, acylation is substantially enhanced through an internal acyl transfer mechanism. Acylation initially occurs on the phenolic oxygen atom, enabled by the intramolecular presence of an amine base, and is followed by an acyl transfer from the oxygen to the nitrogen atom. Fmoc-solid phase synthesis then proceeds, with significantly improved yields for peptide sequences that are difficult to assemble using standard SPPS.

After assembly the peptide is deprotected and cleaved using TFA, with concurrent removal of the Hmb backbone substituent yielding target unprotected peptide in high yields and purity. This backbone protection can also be employed to prevent aspartimide formation, and to improve solubility of protected peptides. In a recent report Hmb groups were introduced on resin-bound peptide via reductive amination, thereby avoiding the use of the more tedious N,O-bis-Fmoc (Hmb)amino acids (Nicolas et al., 1997).

There are two major limitations in the Hmb-backbone protection strategy. Firstly the internal O-to-N acyl transfer only proceeds well for non-hindered cases. When a β-branched amino acid has to be coupled to a $N^\alpha$-Hmb residue other than glycine several hours of heating (80° C.) is required for the rearrangement to proceed. Secondly, this group is only compatible with Fmoc chemistry, and not with the often-preferred BOC SPPS, due to its TFA lability.

The Hmb methodology has demonstrated that backbone substitution can alleviate sequence related assembly problems for Fmoc chemistry. However, for hindered cases it creates additional problems of its own. The methodology would benefit significantly from the development of a more acid stable auxiliary that would allow a faster intramolecular acyl transfer (that does not require heating) and improved assembly of difficult sequences using either Fmoc or Boc SPPS.

This Hmb-backbone substitution approach has led to the recent development of backbone amide linkers (BAL) (Jensen et al., 1998), as shown in Scheme 7.

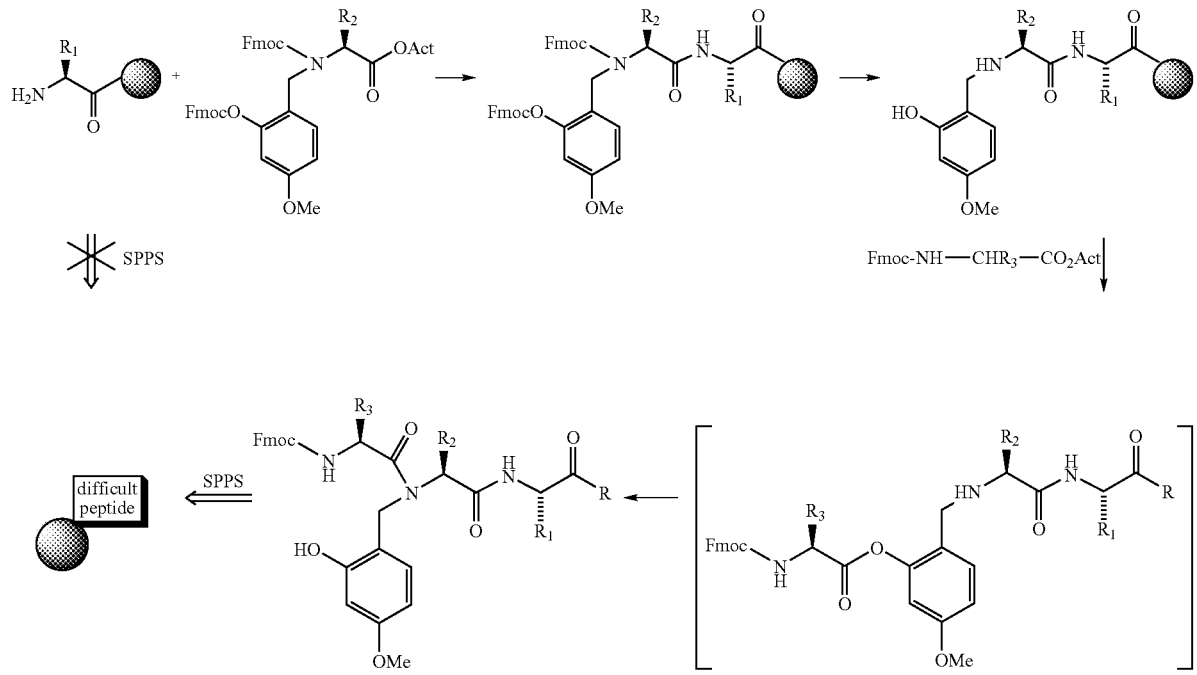

Scheme 6 The use of Hmb-backbone protection during solid phase peptide synthesis ● = solid support

Scheme 7 The Backbone linker approach (BAL)

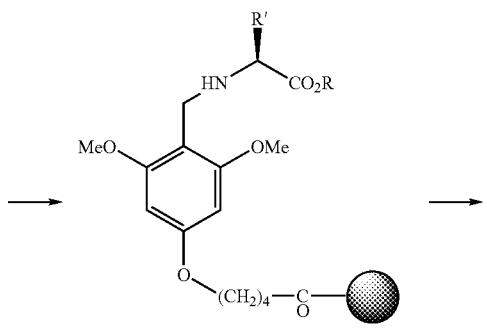

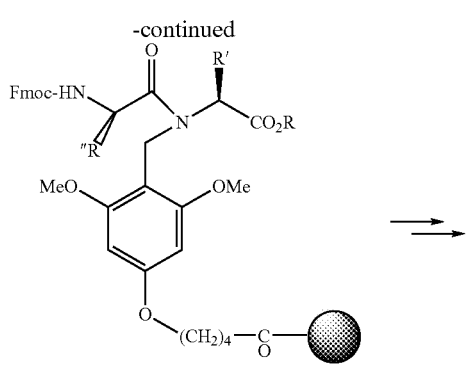

A tris-alkoxybenzyl unit is employed to link a peptide via the backbone amide nitrogen atom to a solid support. The link is cleaved by simple TFA treatment at the end of the synthesis. This linking strategy, in contrast to most other such strategies, does not make use of the C-terminal carboxylic acid, and can, at least in theory, be used on any amide bond. It is thus especially useful for synthesis of C-terminaly modified peptides or for the on-resin synthesis of head-to-tail cyclic peptides. As for the Hmb group, the first limitation lies in the difficulties of acylating the secondary amine to form the "linked" amide bond. A second problem is that standard Fmoc SPPS leads to almost complete diketopiperazine formation at the dipeptide stage. Special protection strategies need to be employed to avoid this problem.

The most valuable auxiliary strategies for peptide ligation, cyclisation or difficult peptide sequence assembly generate unmodified peptide backbones in the final product. There are three critical features in these auxiliary strategies: introduction, acylation and removal, as illustrated in Scheme 8. The prior art strategies have been successfully applied in a limited number of cases. However, applications of these strategies are severely limited by the difficulties encountered in the acyl transfer step and/or the final auxiliary removal. Often the acyl transfer is very slow, or does not proceed at all.

Scheme 8 Reaction steps in the auxiliary strategies

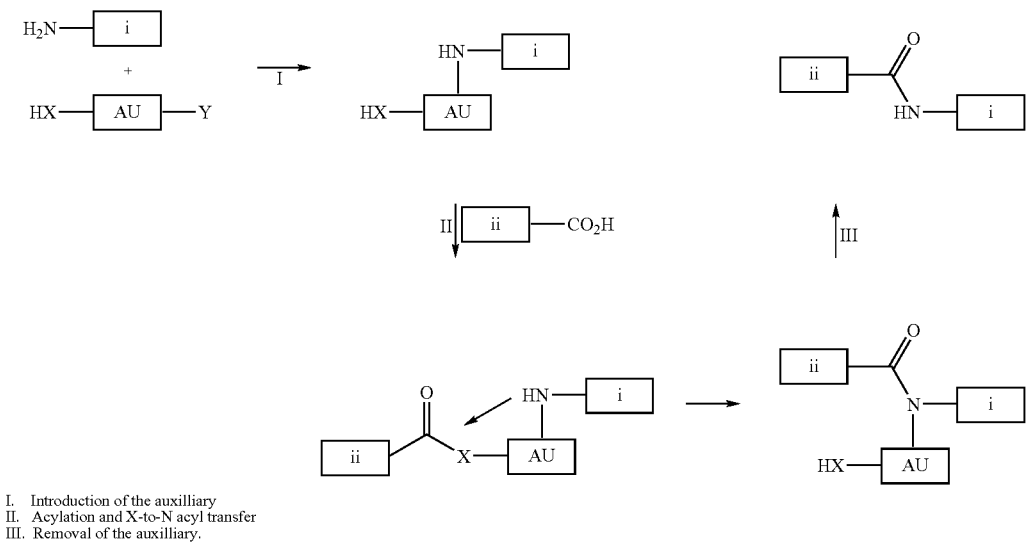

I. Introduction of the auxilliary
II. Acylation and X-to-N acyl transfer
III. Removal of the auxilliary.

It will be clearly understood that, although a number of prior art publications are referred to herein, this reference does not constitute an admission that any of these documents forms part of the common general knowledge in the art, in Australia or in any other country.

There are at least three requirements needed to make the auxiliary approach more versatile:

1. allow generic introduction of the auxiliary at the N atom,
2. allow more effective acylation of the nitrogen atom, and
3. allow removal of the auxiliary after acylation.

This combination of requirements severely limits the design of novel auxiliaries.

We have surprisingly found that a modification of the molecular fragment that links an oxygen or sulfur atom to the nitrogen atom has a strong accelerating effect on the acylation rate of the nitrogen atom, in contrast to prior art examples. In a particularly preferred embodiment, the modification further allows photolytic cleavage of the covalent bond between the acylated nitrogen atom and the remaining molecular fragment that connects the nitrogen atom with the oxygen or sulfur atom.

This approach is particularly useful in the field of peptide synthetic chemistry for applications such as formation of small cyclic peptides, formation of large peptides through native ligation of smaller peptide fragments, synthesis of "difficult" peptides, and backbone-linking to a solid support. The prior art methods are often not effective, ie. they only work for a small number of examples, and thus are not generic. This invention provides a more versatile approach for the synthesis of small cyclic peptides, ligation of peptide segments, backbone protection and linkage of peptide to resin during solid phase peptide assembly.

SUMMARY OF THE INVENTION

This invention describes the use of a new class of auxiliaries that are readily attached to primary amines, for instance at the N-terminus of a peptide, allow for efficient acylation of the nitrogen atom, and in preferred embodiments are readily removed by photolysis. The overall outcome of the use of this auxiliary is the formation of an amide bond. As described below, this new class of auxiliaries has applications in the synthesis of linear peptides and cyclic peptides, in ligation chemistry, and as a backbone linker.

In a first aspect, the invention provides a method of synthesis of linear or cyclic peptides or C-terminal modified peptides, or of on-resin cyclisation of molecules, comprising the step of linking an amine nitrogen atom to a compound of General Formula I

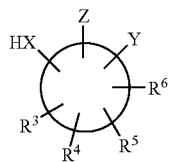

in which the ring optionally comprises one or more heteroatoms selected from the group consisting of nitrogen, oxygen, and sulphur; is of 5 to 7 atoms;

comprises 3 carbon atoms substituted respectively by XH, Z, and Y; and is additionally substituted by groups $R^3$ and $R^4$ when the compound is a 5-membered ring, or is additionally substituted by groups $R^3$, $R^4$, and $R^5$ when the compound is a 6-membered ring, or is additionally substituted by groups $R^3$, $R^4$, $R^5$ and $R^6$ when the compound is a 7-membered ring, in which X is oxygen, sulphur, $CH_2O$, or $CH_2S$—;

Y is an electron-withdrawing group;

Z is any group which allows the formation of a covalent carbon-nitrogen bond;

$R^3$, $R^4$ and $R^5$ are each independently hydrogen, alkyl, substituted alkyl, aryl, substituted aryl, arylalkyl, substituted arylalkyl, heteroaryl, substituted heteroaryl, alkoxy, aryloxy, XH or Y, or a covalent linkage to a solid support, and in which $R^3$ and $R^4$ or $R^4$ and $R^5$ can optionally together with the ring form a 5-, 6-, or 7-membered ring.

Preferably the compound is of general formula II

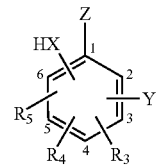

It will be appreciated by those skilled in the art that a degree of symmetry exists in the numbering of atoms in the ring. For the purposes of this specification the carbon atom bearing the substituent Z will be numbered as position 1; thus the numbering scheme shown in Formula II will be used.

Suitable electron-withdrawing groups Y include but are not limited to nitro, ketone, carboxylic ester, amide, nitrile, sulfonamide, sulfoxide, sulfone, sulfonate, fluoride, chloride, bromide and iodide. Other suitable groups are known to those skilled in the art. See for example March (1985).

Z is suitably an aldehyde, alkylalcohol, alkylhalide, ketone, or halogenated $C_{1-3}$alkyl group, in which the halogen is preferably iodine, bromine or chlorine. Preferably the halogenated alkyl group is a methyl group. Suitable Z groups are well known to those skilled in the art. See for example Houben-Weil (1957).

Preferably the XH group is at position 2 or 3 and Y is at any other position; more preferably the XH group is at position 2 and Y is at any other position; most preferably XH is at position 2 and Y is at position 6.

In preferred embodiments of the invention the electron-withdrawing group Y is in position 6. In particularly preferred embodiments, Y is $NO_2$ in position 6. In these cases, the linkage between the compound of general formula II and the amine nitrogen atom is photolabile. Specific compounds within the scope of the invention include, but are not limited to

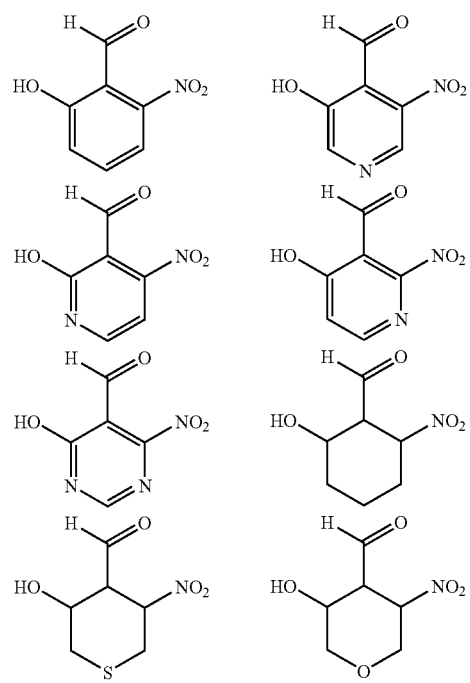

-continued

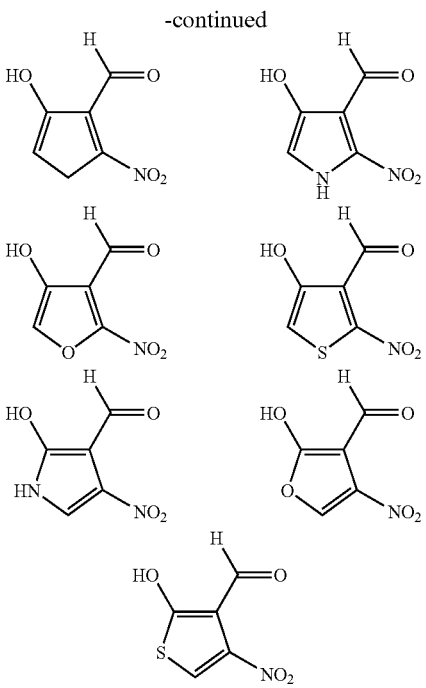

Depending upon the structure of the compound of General Formula I or General Formula II, this compound can provide a reversible auxiliary for formation of amide bonds, with enhancement of the acyl transfer, or a non-reversible auxiliary for the formation of substituted amide bonds, in which acyl transfer is enhanced, which is particularly useful in the synthesis of cyclic peptides. Thus, the compounds of Formula III enable the synthesis of cyclic peptides, large peptides, and difficult peptides which were inaccessible by methods previously available in the art, and allow photolytic removal of the auxiliary after amide bond formation, and compounds of Formula IV enable the synthesis of cyclic peptides, large peptides and difficult peptides containing substituted amide bonds in which the auxiliary is not removed.

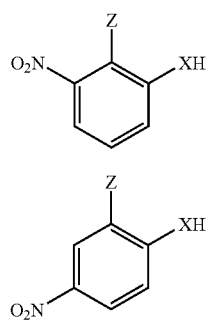

In a second aspect, the invention provides a method of synthesis of a compound selected from the group consisting of linear and cyclic peptides, large peptides with a native peptide backbone, "difficult" peptide sequences, or of backbone linkage for the synthesis of peptides, C-terminal modified peptides, or for on-resin cyclisation, comprising the step of linking a compound of General Formula I, General Formula II, General Formula III or General Formula IV to an amine nitrogen atom. Preferably XH is in position 2 and Y is nitro in position 6. The linkage is then photolabile.

$R^3$, $R^4$, $R^5$ and $R^6$ are preferably independently selected from the group consisting of hydrogen, alkyl, aryl, heteroaryl, hydroxy, alkoxy, aryloxy, and a covalent linkage to a solid support.

In one preferred embodiment, the invention provides a method of synthesis of a cyclic peptide, comprising the steps of a) synthesising a linear peptide to be cyclised, b) linking an auxiliary of the invention to a desired primary amine of the linear peptide, c) activating a desired carboxylic acid to effect cyclisation, and where necessary inducing ring contraction, and optionally d) removing the auxiliary after complete N-acylation.

Ring contraction may be induced by known methods, including but not limited to heating or the addition of metals.

Preferably the auxiliary is of General Formula III, and is removed by photolysis.

A person skilled in the art will appreciate that the above steps can be performed on a solid support, and can be followed by cleavage of the cyclic product from the solid support, and if desired, removal of side chain protecting groups.

A person skilled in the art will also appreciate that the order of steps may be altered in order to obtain the same result. For example, activation of the C-terminal carboxylic acid can be performed in the presence of compounds of Formula II and the cyclisation performed by attaching the auxiliary to the desired amine via the Z-group.

In a second embodiment, the invention provides a method of synthesis of a large peptide with a native peptide backbone, comprising the steps of a) synthesising a set of peptide fragments to be linked to form a large peptide, b) linking an auxiliary of the invention to the primary amine of the first peptide fragment, c) activating the carboxylic acid of the second peptide fragment, d) adding the second peptide fragment to the first peptide fragment and forming a peptide bond between the two fragments, and optionally removing the auxiliary after N acylation is complete.

Preferably the auxiliary is of General Formula III, and is removed by photolysis.

In a third embodiment, the invention provides a method of synthesis of a difficult peptide sequence, comprising the steps of a) linking an auxiliary of the invention to one or more nitrogen atoms in peptide bonds of a peptide linked to a solid support, b) synthesising the complete peptide using standard solid phase synthesis methods, and optionally c) when synthesis is complete, removing the auxiliary.

Preferably the auxiliary is of General Formula III, and is removed by photolysis.

In a fourth embodiment, the invention provides a method of backbone linkage for the synthesis of peptides, comprising the steps of a) using an auxiliary of the invention as a linker linking the α-nitrogen of an amino acid residue in the desired peptide to a solid support, b) assembling the linear peptide using standard solid phase peptide synthesis methods, and optionally c) removing the side chain protecting group, and/or d) cleaving the peptide from the solid support.

The same method can be used for synthesis of C-terminal modified peptides. In this case, the carboxylic acid group of the C-terminal amino acid residue is replaced by a group such as an ester, alkylalcohol, acetal or amide. Other suitable functional carboxylic acid replacement groups are known to those skilled in the art. Preferably Y is nitro in position 6, XH is in position 2 and cleavage is performed by photolysis.

In a fifth embodiment, the invention provides a method of on-resin cyclisation of a linear peptide, comprising the steps of a) using an auxiliary of the invention as a linker linking the α-nitrogen of an amino acid residue in the desired peptide to a solid support, b) synthesising a linear peptide on a solid support, using standard solid phase peptide synthesis methods, c) deprotecting the desired amine and carboxylic acid groups, d) activating the carboxylic acid group to perform cyclisation, and optionally e) deprotecting amino acid side chain groups, and/or f) cleaving the cyclic peptide from the solid support.

Preferably Y is a nitro group in position 6, XH is in position 2, and cleavage is performed by photolysis.

Thus the auxiliaries of the invention may be used for the following purposes:

1. To enable the synthesis of "difficult" cyclic peptides, including small cyclic peptides (up to 10 amino acid residues long). The auxiliary is attached to the primary amine, of the linear peptide, and cyclisation is performed by activating the C-terminal carboxylic acid. Optionally the auxiliary is removed after complete N-acylation.

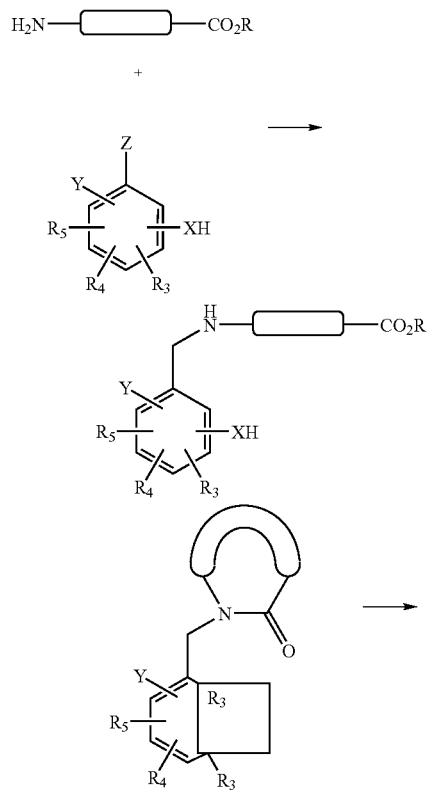

$R^3$, $R^4$ and $R^5$=as described above

☐=Chemical substructure, eg. peptide, peptidometic. These may contain a covalent link to a solid support through an amino acid side chain functionality or though an amide nitrogen atom.

$R_1$=H, alkyl ester, covalent link to a solid support

2. To enable the synthesis of large peptides. The auxiliary is attached to the primary amine of the first fragment, and the carboxylic acid of the second fragment is activated and added to the first fragment. After N-acylation is complete the auxiliary is optionally removed.

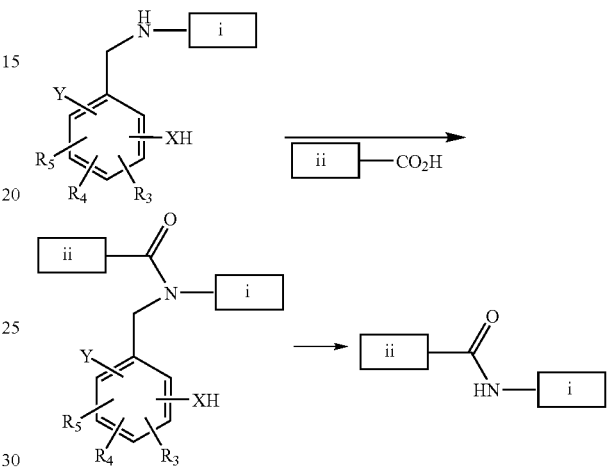

i,ii=molecular fragment, typically peptide. The molecular fragment can be covalently linked to a solid support.

3. To enable synthesis of "difficult" peptide sequences. The auxiliary can be used as a backbone protecting group to avoid aggregation of peptides and enhance solid phase peptide assembly. After introducing the auxiliary, standard SPPS protocols are used for the synthesis of the peptide. Optionally at the end of the synthesis the auxiliary is removed by photolysis.

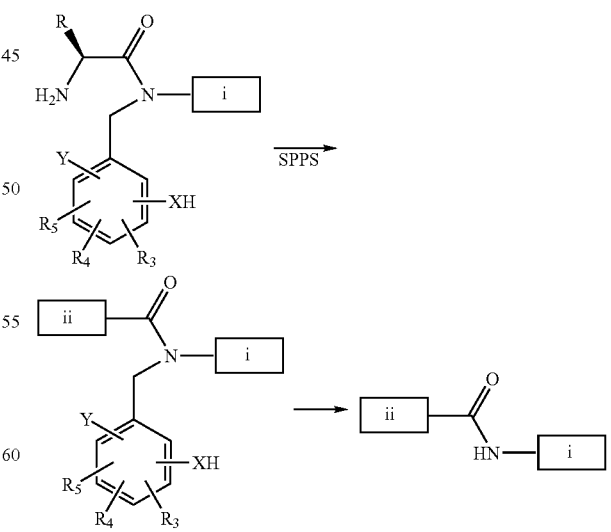

4. To enable backbone linkage for the synthesis of peptides, or C-terminal modified peptides. The auxiliary is employed as a linker to link the α-nitrogen of an amino acid residue to the resin. Standard SPPS protocols can then be employed to assemble the linear peptide. At the C-terminal residue, modified carboxylic acids can be used, such as esters, alcohols, acetals, amides or any other functional group. Alternatively, the linear peptide is cyclised on-resin, after deprotecting the N-terminal amine and the C-terminal carboxylic acids. Side chain deprotection may then be performed prior to photolytic cleavage. (A=carboxylic acid or modified acid, such as ester, acetal, amide, alcohol)

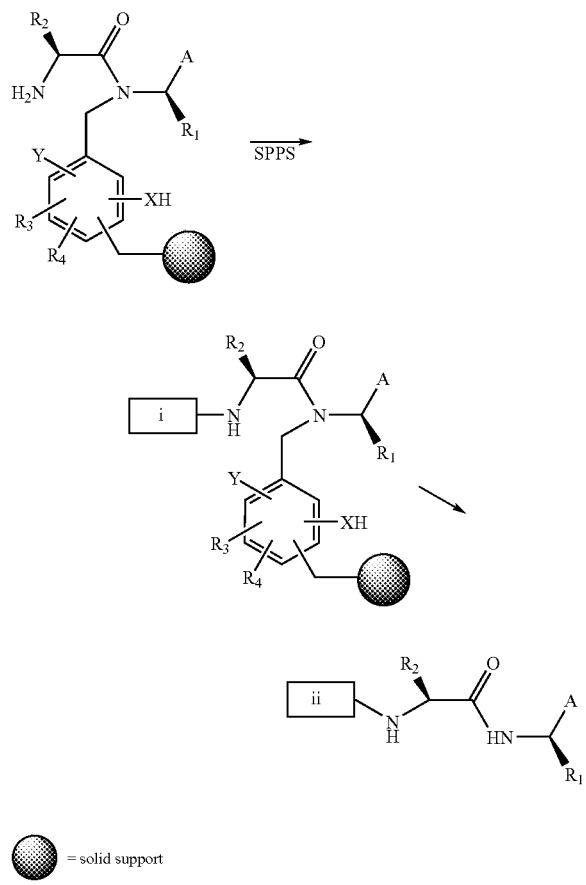

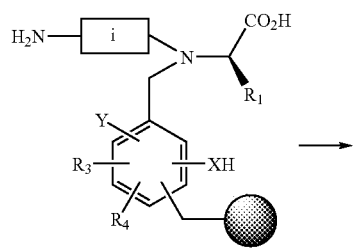

5. To enable backbone linkage for the on-resin cyclisation of molecules. In this case the linear peptide is cyclised on-resin, after deprotection the desired amine and carboxylic acid groups from the resin-bound linear peptide synthesised as described in 4 above. Side chain deprotection may then be performed prior to photolytic cleavage.

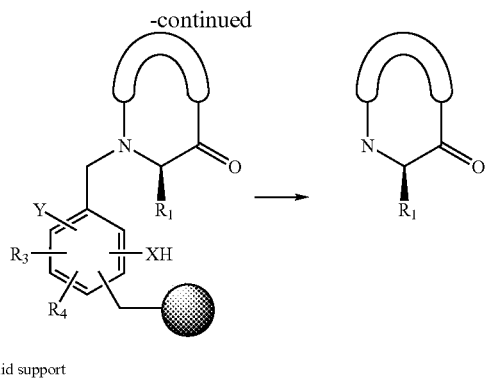

It will be clearly understood that while these reactions are illustrated with the auxiliary of the invention depected as a 6-membered carbocyclic ring, this in no way limits the generality of the invention.

In a third aspect, the invention provides an auxiliary according to any one of General Formulae I, II or III, linked to a support suitable for solid phase peptide synthesis, or to a nitrogen atom of a peptide backbone.

Suitable support resins are well known to those skilled in the art, and include but are not limited to functionalised polystyrene, tentagel resins, and polyethyleneglycol resins such as PEG and PEGA.

The auxiliaries of the invention are suitable for use in combination with other agents useful in the synthesis of cyclic peptides, for example those described in co-pending international application No. PCT/AU99/00081, entitled "Synthesis of Cyclic Peptides," filed on the same day as this application.

The invention also contemplates kits for use in synthesis of peptides, cyclic peptides, or organic compounds, comprising an auxiliary of the invention, or an auxiliary of the invention linked to a solid support, together with one or more other reagents for solid phase peptide synthesis.

The auxiliaries of the invention fulfil the three requirements listed above in a more versatile way, ie. they make a significant improvement in the yield of acylation and they can be readily introduced and optionally removed. We have significantly improved acylation rates (Step II in Scheme 8) by introducing electron-withdrawing substituents on the aromatic ring of the auxiliary. Acylation of our auxiliaries, even in hindered cases, occurs readily with mildly activated amino acids at room temperature. Furthermore, the presence of a nitro group in the ortho position to the alkylamide provides photolability. This combination of improved acylation and facile and clean removal of the auxiliary provides a novel and powerful means to generate amide bonds which is directly applicable to cyclic peptide synthesis, native ligation, the assembly of difficult peptide sequences, and backbone linking.

We have further evaluated the use of these auxiliaries in the synthesis of "difficult" cyclic peptides. We have found surprising improvements compared to the prior art methods. Where prior art methods completely failed to yield the desired product, our strategy produced target cyclic peptides in high yield and purity. The auxiliaries are expected to allow access to many classes of hitherto unknown cyclic peptides.

The auxiliary, linked to a resin, serves as a novel photolabile backbone linker for the solid phase synthesis of organic or peptidic molecules. This linker is especially valuable for the solid phase synthesis of C-terminally modified peptides and cyclic peptides.

Holmes (1997) and U.S. Pat. No. 5,739,386 has described a series of photolabile compounds of the following structure:

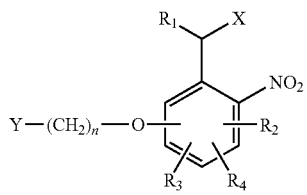

wherein
$R_1$ is hydrogen, C1-C8 alkyl, aryl or arylalkyl; $R_2$, $R_3$ and $R_4$ are each independently hydrogen, C1-C8 alkyl, or $C_1$-$C_8$ alkoxy; X and Y are each independently selected from the group consisting of halogen, —SH, —SP, —OH, —OP, —NH$_2$, —NHP, in which P is a suitable protecting or activating group, and —NR$_5$R$_6$ wherein R$_5$ and R$_6$ are independently selected from the group consisting of hydrogen, alkyl, substituted alkyl, aryl, substituted aryl, heteroaryl, substituted heteroaryl, arylalkyl, substituted arylalkyl; and q is an integer from 1 to 10 and preferably from 1 to 4.

These compounds are used in solid phase chemistry to link molecules to solid supports. The linkers are stable to strong acids and bases, but are labile to UV light at around 350 nm. These compounds differ from those of our invention in at least two ways:

a) The linkers of Holmes are used only as C-terminal linkers, and are not used to facilitate amide bond formation in synthesis of cyclic peptides, peptide ligation or synthesis of difficult sequences. They are not used to link the peptide backbone to a solid support.

b) None of the compounds described by Holmes carries a hydroxy or thiol substituent on the aromatic ring, and indeed such a substituent would have been undesirable for the purposes described by Holmes. The hydroxy-group on the aromatic ring in our compounds is crucial to enable formation of difficult amide bonds.

It will be clearly understood that for the purposes of this specification reference to solid phase peptide synthesis are to be understood to include reference to methods of synthesis of peptidomimetic compounds.

For the purposes of this specification it will also be clearly understood that the word "comprising" means "including but not limited to", and that the word "comprises" has a corresponding meaning.

For the purposes of this specification, the term "monomer" includes compounds which have an amino and carboxy terminus separated in a 1,2, 1,3, 1,4 or larger substitution pattern. This includes the 20 naturally-occurring α-amino acids in either the L or D configuration, the biosynthetically-available amino acids not usually found in proteins, such as 4-hydroxy-proline, 5-hydroxylysine, citrulline and ornithine; synthetically-derived α-amino acids, such as α-methylalanine, norleucine, norvaline, Cα- and N-alkylated amino acids, homocysteine, and homoserine; and many others as known to the art. It also includes compounds that have an amine and carboxyl functional group separated in a 1,3 or larger substitution pattern, such as-β-alanine, γ-amino butyric acid, Freidinger lactam (Freidinger et al, 1982), the bicyclic dipeptide (BTD) (Freidinger et al, 1982; Nagai and Sato, 1985), aminomethyl benzoic acid (Smythe and von Itzstein, 1994), and others well known to the art. Statine-like isosteres, hydroxyethylene isosteres, reduced amide bond isosteres, thioamide isosteres, urea isosteres, carbamate isosteres, thioether isosteres, vinyl isosteres and other amide bond isosteres known to the art are also useful for the purposes of the invention. Thus the word "peptide" as used herein encompasses peptidomimetic compounds. Optionally the peptide may be protected with one or more protecting groups of the type used in the art (see for example Bodanszky, M., (1984), "*Principles of Peptide Synthesis*", Springer-Verlag, Heidelberg).

The solid support may be of any type used for solid phase synthesis of peptides, peptidomimetics, oligonucleotides, oligosacharides or organic molecules. The solid support may be in the form of a bead, a pin or another such surface which is suitable for use in solid phase synthesis. A wide variety of suitable support materials are known in the art. See for example Meldal (1997). Commercially-available polystyrene supports, including aminomethyl-polystyrene, benzhydrylaminepolystyrene, polyethyleneglycol-polystyrene are especially suitable.

Coupling methods to form peptide bonds are also well known in the art. See for example Albericio and Carpino (1997).

BRIEF DESCRIPTION OF THE FIGURES

In FIG. 1, VSILETKIYGT is SEQ ID NO:35.

DETAILED DESCRIPTION OF THE INVENTION

Figures 1, 2:
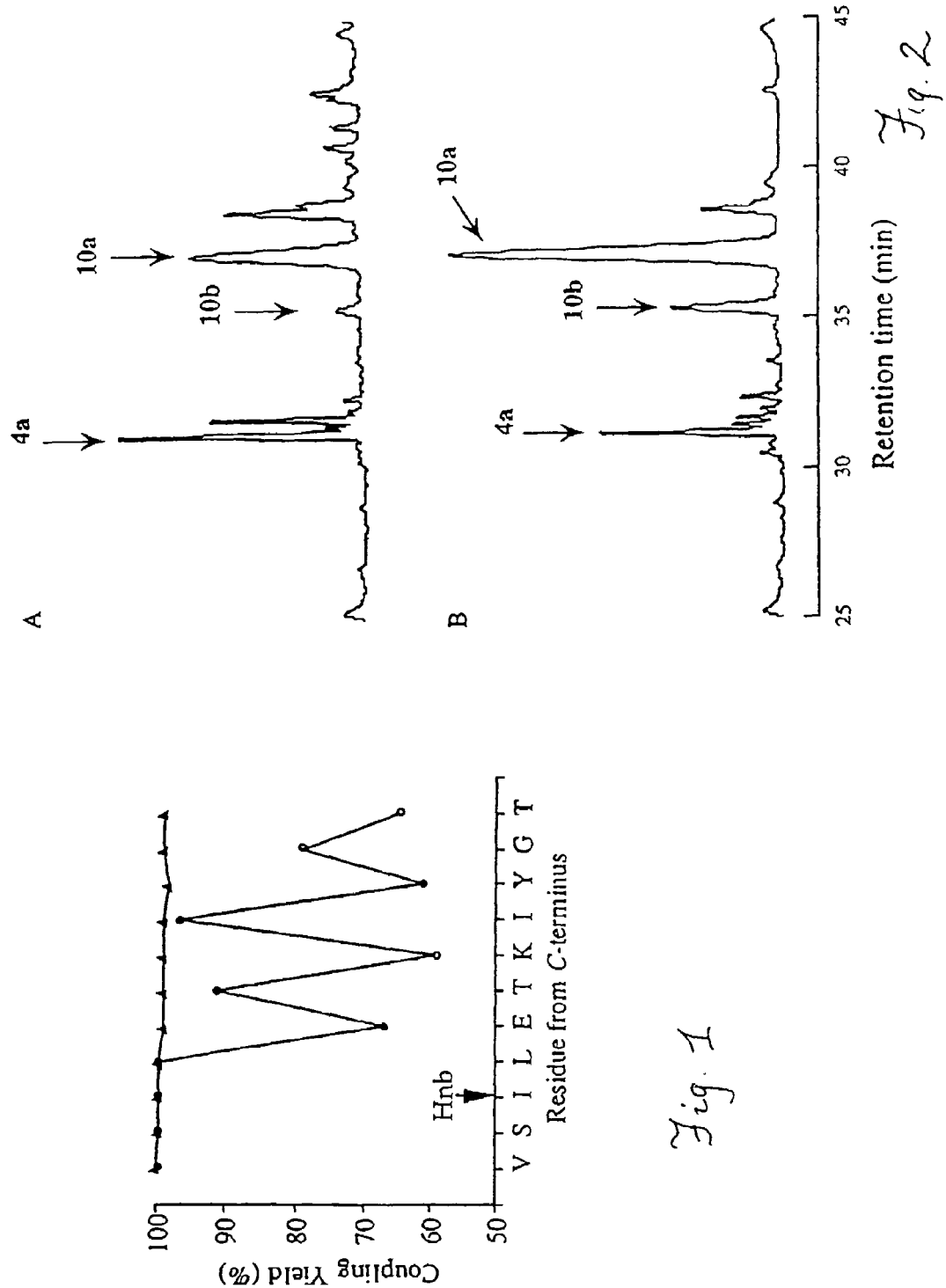
FIG. 1 shows a comparison of the coupling yields for the Fmoc chain-assembly of STA-91 (699-709) using: (A) Standard 10 min HBTU coupling protocols (-o-), which resulted in an average coupling yield of 83%; and (B) Hnb-assisted 10 min HBTU coupling protocols, with the incorporation of the Hnb auxiliary at Ile$^{707}$ (-Δ-). Average coupling yield 99.6%.
FIG. 2 shows the results of HPLC analysis of cyclisation of linear peptide 4a A) after 3 h at rt and B) 1 h heating to 65° C. in the presence of excess DIEA. The solutions were dried under high vacuum, dissolved in 50% aqueous acetonitrile and were loaded directly onto a Vydac reversed-phase C-18 (5 μm, 300 Å, 0.46×25 cm) HPLC column. The products were separated using a linear 0-80% buffer B gradient over 40 min at a flow rate of 1 mL/min.

The invention will now be described in detail by way of reference only to the following non-limiting examples.

Abbreviations used herein are as follows:

| | |
|---|---|
| AcOH | Acetic acid |
| BOC | N$_\alpha$-tert-butoxycarbonyl |
| BOP | Benzotriazole-1-yl-oxy-tris-(dimethylamino)-phosphonium-hexafluorophosphate |
| $^t$Bu | tert-Butyl |
| calcd | calculated |
| DCM | dichloromethane |
| DIEA | diisopropylethylarnine |
| DMF | N,N-dimethylformamide |
| eq | equivalent |

-continued

| | |
|---|---|
| ES-MS | Electrospray Mass Spectrometry |
| LC/MS | Liquid Chromatography linked to Mass Spectrometry |
| Fmoc | 9-Fluorenylmethyloxycabonyl- |
| HBTU | O-benzotriazole-N,N,N',N'-tetramethyluronium hexafluorophosphate |
| HF | anhydrous hydrogen fluoride |
| NMR | Nuclear magnetic resonance |
| ONBS | o-nitrobenzene-sulfonamide |
| Pam | Phenylacetamidomethyl |
| PMC | 2,2,5,7,8-pentamethylchroman-6-sulfonyl |
| RP-HPLC | Reversed phase high-performance liquid chromatography |
| RT | room temperature |
| SPPS | Solid phase peptide synthesis |
| TFA | trifluoroacetic acid |
| UV | Ultraviolet |

Materials and Methods

Chlorotrityl resin (sv=0.92 mmol/gr) was purchased from PepChem (Tubingen, Germany). All Wang resins and $N_\alpha$-tert-butoxycarbonyl (BOC)-L-amino acids were peptide synthesis grade purchased from Auspep (Melbourne Australia), Novabiochem (San Diego) or Peptide Institute (Osaka, Japan). Pam resins were purchased from Applied Biosystems (Foster City, Calif.). Dichloromethane (DCM), diisopropylethylamine (DIEA), N,N-dimethylformamide (DMF), and trifluoroacetic acid (TFA) were obtained from Auspep (Melbourne, Australia). p-Cresol, p-thiocresol, 3-nitrophenol, polyphosphoric acid, hexamethylenetetramine were purchased from Aldrich or Fluka (Sydney, Australia). HPLC grade acetonitrile was purchased from Millipore-Waters (Sydney, Australia). 2-(1H-Benzotriazol-1-yl)-1,1,3,3-tetramethyluronium hexafluoro-phosphate and Benzo-triazole-1-yl-oxy-tris-(dimethylamino)-phosphonium-hexafluorophosphate was purchased from Richelieu Biotechnologies (Quebec, Canada). Deionised water was used throughout and was prepared by a Milli-Q water purification system (Millipore-Waters). Screw-cap glass peptide synthesis reaction vessels (20 mL) with sintered glass filter frit were obtained from Embell Scientific Glassware (Queensland, Australia). Argon, helium and nitrogen (all ultrapure grade) were from BOC Gases (Queensland, Australia).

$^1$H NMR and $^{13}$C NMR spectra were recorded on a Varian 300 MHz Gemini in $CD_3OD$, and chemical shifts are reported in parts per million (ppm) downfield from $(CH_3)_4Si$.

Reversed phase high-performance liquid chromatography (RP-HPLC) was performed on a Waters 600E solvent delivery system equipped with a 484 absorbance detector at 214 nm or 230 nm (Applied Biosystems Inc.) or on a Hewlet Packard HP1100 system equipped with Diode-Array detector. HPLC data were collected using Turbochrome or HPLC 2D Chemstation software. RP-HPLC was performed on a Zorbax microbore (SB-C18, 2.1 mm×5 cm) column, a Vydac C-18 analytical (5 mm, 0.46 cm×25 cm) column or a Vydac preparative C-18 (10 mm, 2.2 cm×25 cm) column. Chromatographic separations were achieved using linear gradients of buffer B in A (A=0.1% aqueous TFA; B=90% $CH_3CN$, 10% $H_2O$, 0.09% TFA) at a flow rate of 0.25 mL/min (microbore), 1 mL/min (analytical) and 8 mL/min (preparative).

Mass spectra were acquired on a PE-Sciex API-III triple quadrupole mass spectrometer equipped with an Ionspray atmospheric pressure ionization source. Samples (10 µL) were injected into a moving solvent (30 µL/min; 50/50 $CH_3CN$/0.05% TFA) coupled directly to the ionisation source via a fused silica capillary interface (50 mm i.d.×50 cm length). Sample droplets were ionized at a positive potential of 5 kV and entered the analyser through an interface plate and subsequently through an orifice (100-120 mm diameter) at a potential of 80 V. Full scan mass spectra were acquired over the mass range of 400 to 2000 Daltons with a scan step size of 0.1 Da. Molecular masses were derived from the observed m/z values using the MacSpec 3.3 and Biomultiview 1.2 software packages (PE-Sciex Toronto, Canada). Calculated theoretical monoisotopic and average masses were determined using the MacBiospec program (PE-Sciex Toronto, Canada). LC/MS runs were carried out using a linear gradient on a 140B ABI dual syringe pump solvent delivery system and a Zorbax reversed phase C-18 (SB, 2.1 mm×5 cm)) column at a flow rate of 150 µL/min. Samples (typically 5 µL of 1 mg/mL solution) were loaded directly on the column and the eluent directly connected to the mass spectrometer via a 30 cm, 75 mm i.d. fused silica capillary. The application of Turbo Ionspray™ (5 L/min N2 at 500° C.) allowed the introduction of the total eluent without splitting and loss in sensitivity. Acquisition parameters were as described above.

Examples 1 to 5

Introduction of the Auxiliaries

Our synthetic approach for introducing the auxiliary is depicted in Scheme 9. In brief, there are two reported pathways that provide access to the N-substituted linear peptides:

1. A first, and most common route, makes use of a reductive alkylation of the N-terminal primary amine with the aldehyde. Initially the aldehyde is added in excess to the resin-bound peptide. After imine formation is complete, as assessed by ninhydrin reaction, a solution of $NaBH_4$ in DMF/MeOH (2/1) or $NaBH_3CN$ in DMF/MeOH (1/1) containing 5% acetic acid is added to reduce the imine and generate the —$CH_2$— link between the auxiliary and the amine.

Scheme 9 Introduction of the auxiliaries

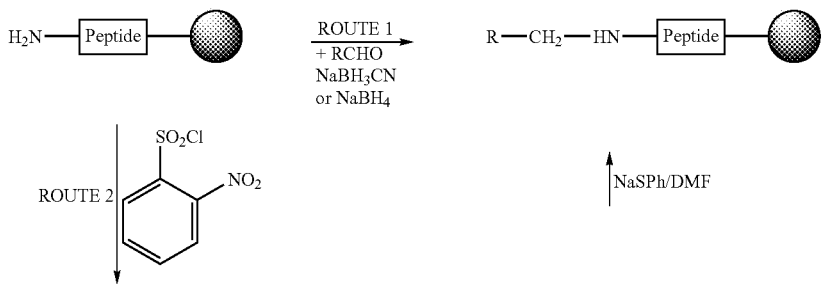

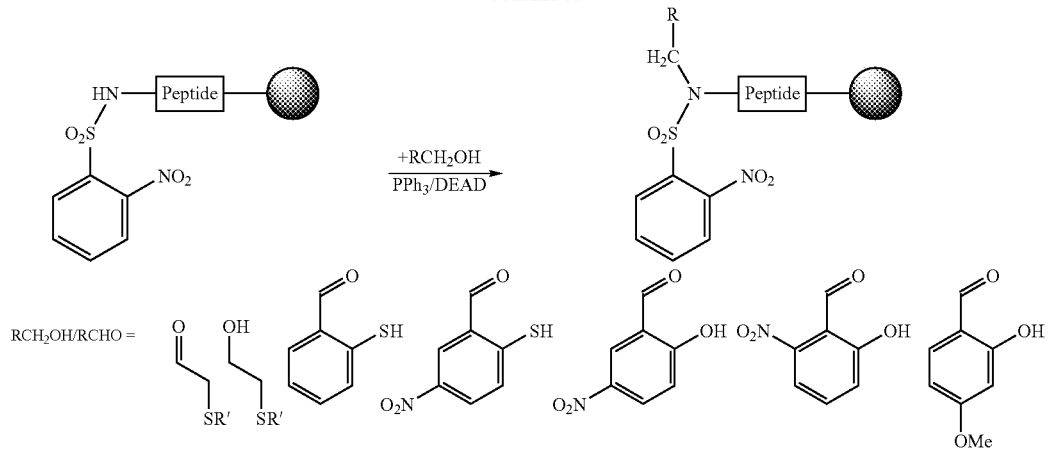

2. In a second route an o-nitrobenzene-sulfonamide (ONBS) is prepared from the corresponding sulfonylchloride and the amine. A Mitsonobu-type alkylation, using the auxiliary alcohol, establishes the link with the amine. Finally the ONBS-group is removed using PhSNa in DMF. This three-step process is also known as the Fukuyama reaction.

Example 1

Synthesis of HS—$(CH_2)_2$-Tyr-Arg-Phe-Gly-OH. (SEQ ID NO:1)

Synthesis was performed on Fmoc-Gly-WANG resin (0.36 mmol/g). The tetrapeptide Tyr-Arg-Phe-Gly (SEQ ID NO:21) was assembled using stepwise Fmoc-SPPS, with alternating HBTU coupling and piperidine deprotection as follows:

Coupling 2 mmol Fmoc-amino acid (4 equivalents) were dissolved in DMF (4 mL) and 2 mmol HBTU added to the solution together with DIEA (400 µL). After 1 minute preactivation the solution was added to the amino-resin. The reaction was left for 10 minutes and ninhydrin test performed on a small resin sample to measure the amount of remaining free amine. If the measured amount of free amine was more than 0.5%, the reaction was left longer (30 minutes) and if necessary repeated. The resin was then washed several times with DMF.

Deprotection

The Fmoc protected resin (0.5 mmol) was treated with a solution of Piperidine/DMF (1/1) (4 mL) for 2 minutes. The resin was drained and the piperidine treatment repeated. The resin was then washed several times with DMF before the next coupling step was commenced.

The Tyr(Bu)-Arg(PMC)-Phe-Gly-WANG resin (SEQ ID NO:2) (1 g) was then treated with S-(p-methylbenzyl)-2-mercapto-acetaldehyde (58 mg; 0.32 mmol, Bitan et al, 1997) dissolved in MeOH/DMF/AcOH (47/47/5) (6 mL). After 5 min stirring 60 mg of NaBH$_3$CN was added and the mixture left for 60 minutes. The reductive alkylation step was then repeated once more to ensure complete reaction. The resin was washed several times with DMF/MeOH, MeOH/DCM and DCM and finally air dried.

HF Cleavage 1 g of resin was treated with 1 mL of p-cresol and 9 mL HF at 0° C. for 1 hour. The HF was evaporated in vacuo and the residue triturated with cold diethylether (20 mL). The ether was filtered off and the precipitated dissolved in a small amount of water. The solution was then loaded directly on to an HPLC column (Vydac, C18 reverse phase 2.1×25 cm) for HPLC purification of the products (buffer A: water, 0.1% TFA; buffer B: acetonitrile/water 1/1, 0.09% TFA) (100% A to 80% B in 60 min). The HS—$(CH_2)_2$—NH—CH($CH_2$PhOH)—CO-Arg-Phe-Gly-OH was isolated and lyophilised, yielding 70 mg of white powder (45% yield), Mr 601.5, calcd for $C_{28}H_{39}N_7O_6S$: 601.27.

Example 2

Synthesis of N-(5-nitro-2-mercaptobenzyl)-Tyr-Arg-Phe-Gly-OH (SEQ ID NO:3)

Tyr(Bu)-Arg(PMC)-Phe-Gly-WANG resin (SEQ ID NO:2) was prepared as described in Example 1.

120 mg of 2,2'-dialdehyde-4,4'-dinitro-[diphenyldisulfide] (Fries and Brothuhn, 1923) (0.33 mmol) was dissolved in MeOH/DMF/AcOH (47/47/5) (3 mL) and the solution added to the resin. After 5 minutes, 100 mg NaBH$_3$CN (1.6 mmol) was added and the solution stirred for 15 hours. The resin was washed with DMF (3×) and MeOH/DCM 1/1 (3×).

TFA Cleavage 700 mg of resin was treated with 10 mL TFA/H$_2$O (95/5) for 1 hour at room temperature. The TFA was removed in vacuo and the residue dissolved in HPLC buffers A/B 1/1 (5 mL). The solution was then loaded directly on to an HPLC column and purification of the product performed as in Example 1. 25 mg N-(5-nitro-2-mercaptobenzyl)-Tyr-Arg-Phe-Gly-OH (SEQ ID NO:3) were obtained from lyophilisation (20% yield), Mr 708.4 (calcd for $C_{33}H_{40}N_8O_8S$: 708.27).

Example 3

Synthesis of HS—$(CH_2)_2$-Ala-Phe-Leu-Pro-Ala-OH (SEQ ID NO:4)

Ala-Phe-Leu-Pro-Ala-WANG resin (SEQ ID NO:5) was prepared starting from Fmoc-Ala-WANG resin (0.44 mmol/gram) using standard Fmoc-SPPS protocols, with HBTU coupling and piperidine deprotection as described in Example 1. To 500 mg of this resin, a solution of 300 mg o-nitrobenzenesulfonylchloride in DMF (4 mL) containing DIEA (200 µL) was added. After 30 minutes, the resin was drained and washed with DMF (3×). The resin was mixed with a solution of S-(p-methylbenzyl)-2-mercaptoethanol (270 mg, 1.5 mmol) in DCM (5 mL). Triphenylphosphine (393 mg, 1.5 mmol) and diethylazodicarboxylate (DEAD, 261 mg, 1.5 mmol) were premixed in DCM (5 mL). After 1 minute, the solution was added to the resin and the reaction left for 30 minutes. The resin was washed with DCM (3×) and DMF (3×). The resin was further treated with a solution of NaSPhe (200 mg, 1.5 mmol) in DMF (4 mL) for 30 minutes. The resin was washed with DMF (3×) and MeOH/DCM (3×) and air dried.

HF Cleavage 500 mg of resin was cleaved using HF/p-cresol/p-thiocresol (9/1/1) (10 mL) (1 hour at 0° C.) and was worked up as described in Example 1. The crude residue was dissolved in buffers A/B (1/1) and purified on HPLC yielding HS—(CH$_2$)$_2$—NH—CH(CH$_3$)—CO-Phe-Leu-Pro-Ala-OH (SEQ ID NO:6) (25 mg, 22% yield). Mr: 577.1 (calc for C$_{28}$H$_{43}$N$_5$O$_6$S: 577.29)

Example 4

Synthesis of N-(2-hydroxy-5-nitrobenzyl)-Ala-Phe-Leu-Pro-Ala-OH (SEQ ID NO:7)

Fmoc-Ala-trityl resin (0.4 mmol/gr) was first prepared from trityl resin (0.96 mmol/gr) using protocols provided by Pepchem (Tubingen, Germany). Ala-Phe-Leu-Pro-Ala-Trityl resin (SEQ ID NO:36) was assembled using standard Fmoc SPPS protocols, as in Example 1. This resin (0.5 gr) was further treated with a solution of 2-hydroxy-5-nitrobenzaldehyde (115 mg, 0.7 mmol) and AcOH (20 μL) in DMF (2 mL). After 5 minutes the resin was drained and a second aldehyde treatment was performed. The resin was drained, and washed copiously with DMF until eluent was colourless. A solution of NaBH$_4$ (150 mg, 4 mmol) in DMF/MeOH 3/1 (4 mL) was added and the resin stirred for 10 minutes. The resin was drained, washed with DMF/MeOH 1/1, DCM/MeOH 1/1 and DCM and air dried.

TFA Cleavage

The resin was treated with DCM (10 mL) and TFA (100 μL) for 1 hour. The solution was evaporated, buffer B (3 mL) was added and the resin filtered off. The solution was loaded directly on to a preparative HPLC column and HPLC purification performed using a 2% gradient (from 90% A to 10% A in 40 minutes). After lyophilisation N-(2-hydroxy-5-nitrobenzyl)-Ala-Phe-Leu-Pro-Ala-OH (SEQ ID NO:7) (114 mg) was isolated as a white powder (85% yield), Mr: 668.2 (calcd for C$_{33}$H$_{44}$N$_6$O$_9$: 668.32).

Example 5

Synthesis of N-(2-hydroxy-6-nitrobenzyl)-Ala-Phe-Leu-Pro-Ala-OH (SEQ ID NO:8)

The linear peptide was synthesised on trityl resin as described in example 4, but employing 2-hydroxy-6-nitrobenzaldehyde (Harayama et al, 1994). After lyophilisation N-(2-hydroxy-6-nitrobenzyl)-Ala-Phe-Leu-Pro-Ala-OH (SEQ ID NO:8) (85 mg) was isolated as a white powder (63% yield), Mr 668.2, calcd for C$_{33}$H$_{44}$N$_6$O$_9$: 668.32).

Example 6

Acylation Rate of the Arylamine

The most important factor limiting the use of the prior art methods was the O-to-N or S-to-N acyl transfer step. One of the parameters which we envisaged would have a large impact on the rate of acyl transfer was the activation of the intermediate oxy- or thioester bond. With this in mind we focussed on the following auxiliary modifications:

Introduction of a nitro substituent on the aromatic ring of the auxiliary. Nitrophenyl esters react more readily with nucleophiles when compared to phenyl esters.

Thio-esters versus oxy-esters. In previous work in our laboratory we found that under the same conditions both esters hydrolyse at the same rate. We have included both phenols and thiophenols in our set of N-substituents.

To compare the rate of acyl transfer we carried out the reactions shown in Scheme 10.

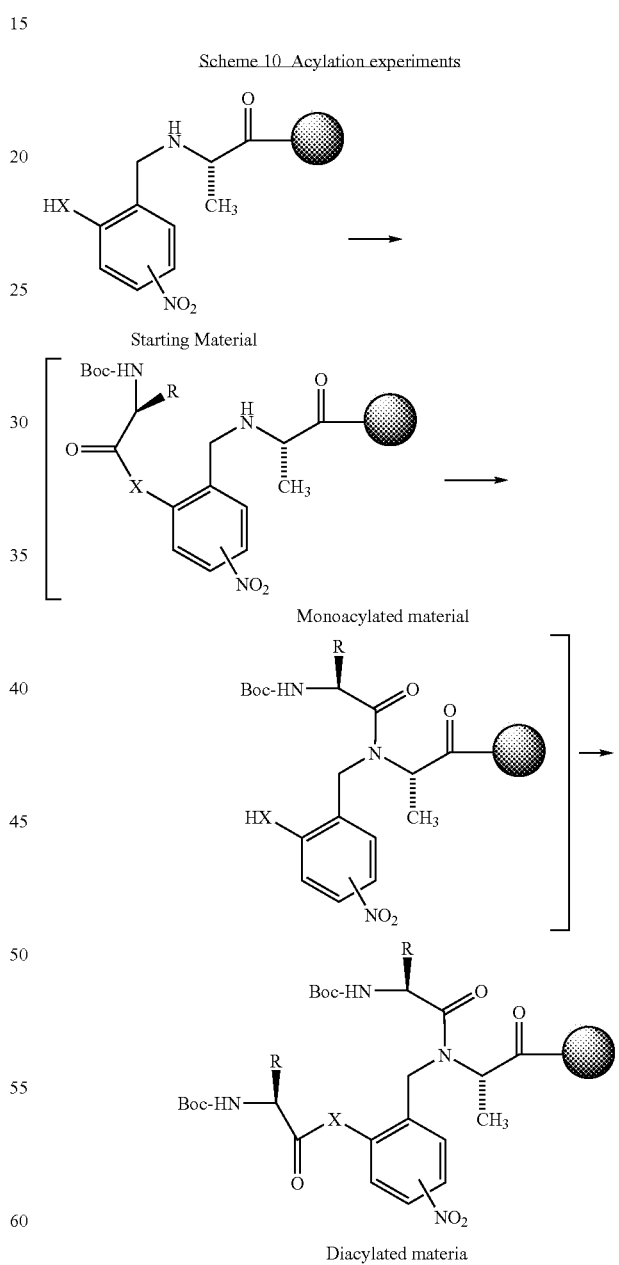

Scheme 10. Acylation experiments

A tripeptide (Ala-Gly-Phe) was assembled on WANG-resin, and the selected range of aldehydes introduced via reductive amination. Each N-substituted tripeptide was then subjected to acylation by mixing the resin with a solution of HBTU-activated Boc-amino acid (Boc-Ala-OH, Boc-Phe-OH or Boc-Val-OH). The general reaction pathway was as follows: acylation of the N-substituted tripeptide occurs initially on the phenol oxygen (or sulfur) atom. The acyl group subsequently migrates to the nitrogen atom. The liberated phenol (or thiophenol) functionality was then acylated a second time.

We included as a control the 2-chloro-4-nitrobenzyl substituent. Due to the absence of the alcohol we expected that acylation directly on to the secondary amine, will be much slower then for the phenol/thiophenol cases. The results are summarized in Table 1.

Valine required 60 minutes to achieve 82% diacylation. In other words, acylation at the nitrogen atom was >80% complete after 60 min. when Boc-Valine was used. As a comparison, in a very similar study acylation of the alpha-nitrogen atom of N-[2-hydroxy-4-methoxybenzyl]-alanine with Fmoc-valine was still incomplete after 24 hours. In the case of acylation of the 2-mercapto-5-nitro-derivative with Boc-Alanine, diacylation only reaches 37% after 60 min.; from comparison with the other results we ascribe this to hydrolysis of the highly reactive and less hindered ester bond in the diacylated product during work-up.

TABLE 1

Distribution of N-terminal acylation products on the N-[auxiliary]-AGF sequence

| | | \multicolumn{9}{c}{N-terminal Acylation Products (%)[a]} |
| Auxiliary | t (min) | Alanine | | | Phenylalanine | | | Valine | | |
| | | unreacted | mono-acylated | diacylated | unreacted | mono-acylated | diacylated | unreacted | mono-acylated | diacylated |
|---|---|---|---|---|---|---|---|---|---|---|
| 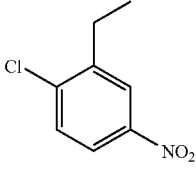 | 30 | >98 | ND | ND | >98% | ND | ND | >98% | ND | ND |
| 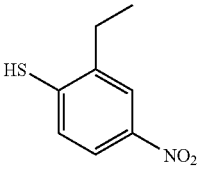 | 1 | 33 | 40 | 27 | 10 | 57 | 33 | 18 | 58 | 24 |
| | 10 | 5 | 77 | 18 | 4 | 12 | 84 | 8 | 19 | 73 |
| | 60 | 3 | 60 | 37 | ND | 11 | 89 | 3 | 9 | 88 |
| 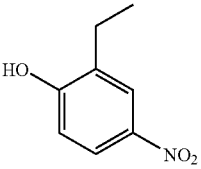 | 1 | 4 | 8 | 88 | 2 | 17 | 81 | 26 | 47 | 27 |
| | 10 | 2 | 2 | 96 | ND | 2 | 98 | 4 | 19 | 77 |
| | 60 | ND | 1 | 99 | ND | <1 | 99 | 2 | 15 | 83 |
| 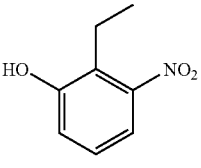 | 1 | ND | 35 | 65 | 4 | 21 | 75 | 48 | 46 | 6 |
| | 10 | ND | 27 | 73 | ND | 18 | 82 | 7 | 63 | 30 |
| | 60 | ND | 16 | 84 | ND | 21 | 79 | 4 | 14 | 82 |

[a] ND indicates product not detected.

The following conclusions can be drawn from these

1. The presence of the alcohol/thiol function at the ortho position of the aromatic ring dramatically increases the rate of acylation of the substituted amine. Under the same acylation conditions, the ortho-chloro "auxiliary" did not undergo acylation at the secondary amine site.

2. The presence of an alcohol/thiol function in combination with a nitro substituent on the aromatic ring ensures very rapid acylation of the secondary amine. For most of the cases studied >70% diacylated product was formed after 10 minutes. Acylation of the 2-hydroxy-6-nitro-derivative with Boc- 3. The position of the nitro-group on the ring does not seem to play a major role, although small differences can be observed. Substituting oxy-ester for thioester does not significantly alter the rate.

Experimental

The Ala-Gly-Phe sequence was assembled on Wang resin (0.1 mmol, Novabiochem) using standard Fmoc/HBTU protocols. Auxiliaries were introduced as described in Examples 2, 4 and 5. Each resin was then distributed into three portions in a separate reaction vessels, and swelled in DMF for 10 min. Three equivalents of Boc-Ala-OH, Boc-Phe-OH, or Boc-Val-OH were coupled to Ala-Gly-Phe-resin using 0.99 equivalents of HBTU with 4 equivalents of DIEA. Samples (10-15 mg) were removed after 1 minute, 10 minutes and 60 minutes, immediately drained, washed with 1:1 DCM:MeOH, and dried. Samples were then cleaved with 250 mL of 97% TFA at room temperature for 1 h. The TFA was evaporated with a stream of nitrogen and the product dissolved in 50% B (100 mL). The sample was centrifuged and the supernatant collected, then analysed by RP-HPLC and ES-MS or LC/MS. The relative yields of unreacted starting material, monoacylated and diacylated product for each experiment were calculated by integrating the HPLC signals in the corresponding chromatogram.

Example 7

Evaluation of Auxiliary Acyl Transfer Efficiency

In this example we demonstrate the improved O→N acyl transfer kinetics of our auxiliaries when compared to prior art auxiliaries such as the 2-hydroxy-4-methoxybenzyl auxiliary. The N-acylation product is formed from the ligation of one residue with a resin bound peptide. This example thus also serves as an example of improved ligation using the auxiliaries of this invention.

In order to establish the relative O→N acyl transfer efficiencies of the 2-hydroxy-4-methoxybenzyl, the 2-hydroxy-5-nitrobenzyl and the 2-hydroxy-6-nitrobenzyl auxiliaries, a series of 2-(1H-benzotriazol-1-yl)-1,1,3,3-tetramethyluronium hexafluorophosphate (HBTU)-mediated amino acid acylation experiments were carried out. Initially, the ortho-oxygen atom of the benzyl auxiliary is acylated by the HBTU-activated amino acid to yield 2. Following this, the acyl group then migrates to the $N^\alpha$-nitrogen atom to form an amide bond 3. The ortho-oxygen in the presence of excess acylating agent then becomes available for acylation for a second time with diacylation leading to 4 (Scheme 11).

The resin-bound tripeptide, Ala-Gly-Phe, was assembled using standard Fmoc-SPPS protocols on chlorotrityl resin, and the benzaldehyde auxiliary incorporated by reductive alkylation. The peptide-resin of each $N^\alpha$-auxiliary substituted peptide was divided into three separate portions, and subjected to acylation with 3 equiv of 0.5 M HBTU-activated Fmoc-Ala, Fmoc-Phe, or Fmoc-Val in DMF. Aliquots were removed for analysis after 1, 10, and 60 min. Following reaction, the peptide-resins were washed with DMF, base-treated with piperidine/DMF/water, washed with DMF then DCM, dried, and cleaved with 0.5% TFA in DCM for 30 min. These base treatments were employed to remove O-aryl esters present (2 and 4), prior to TFA cleavage, in order to distinguish between auxiliary (O) and $N^\alpha$-amino acylation (Scheme 11). The products were then identified by ES-MS or LC/MS analysis and quantified by reversed phase-HPLC peak integration. The results are shown in Table 2.

Initially, to determine the extent of direct $N^\alpha$-acylation using HBTU-activated amino acids, acylation experiments were carried out with a control auxiliary, $N^\alpha$-2-chloro-5-nitrobenzyl. As expected, no appreciable amount (<1%) of secondary $N^\alpha$-acylation had occurred after 30 min with HBTU-activated alanine, phenylalanine, or valine. Next, the presence of an "inactivated" ortho-hydroxy group as with the Hmb auxiliary (1a) was examined. We found the formation $N^\alpha$-acylated products did occur by acyl transfer, albeit at relatively slow rates. Hmb-mediated acyl transfer proceeds at a reasonable rate for alanine after 1 h (92%), but the transfer efficiency diminishes sharply with increasing steric bulk on amino acid side-chains, as with phenylalanine (48%) or valine (12%). These observations agree well with acylation studies carried out by others, and also re-emphasises the need for N-terminal auxiliaries for SPPS with improved acyl transfer efficiency.

In contrast to the limb auxiliary (1a), the presence of an ortho-hydroxyl group in combination with the electron-withdrawing nitro substituent on the benzyl ring of an auxiliary significantly enhances acyl capture and transfer efficiency. Acyl transfer ($N^\alpha$-acylation) mediated by the

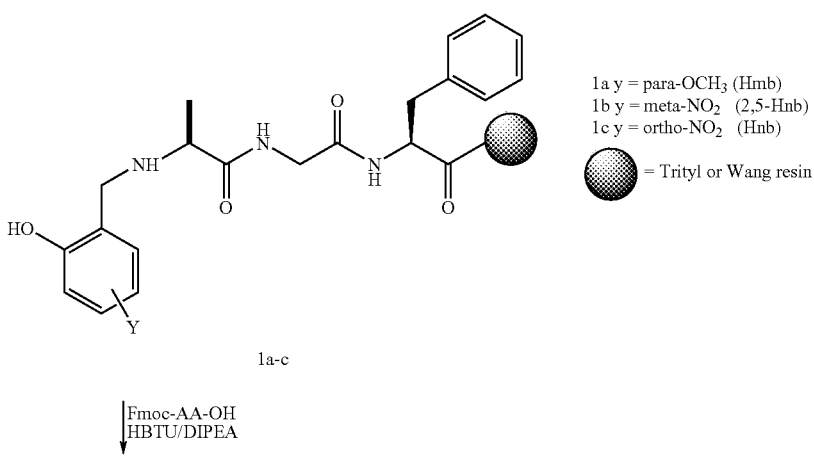

Scheme 11

1a y = para-OCH$_3$ (Hmb)
1b y = meta-NO$_2$ (2,5-Hnb)
1c y = ortho-NO$_2$ (Hnb)

= Trityl or Wang resin

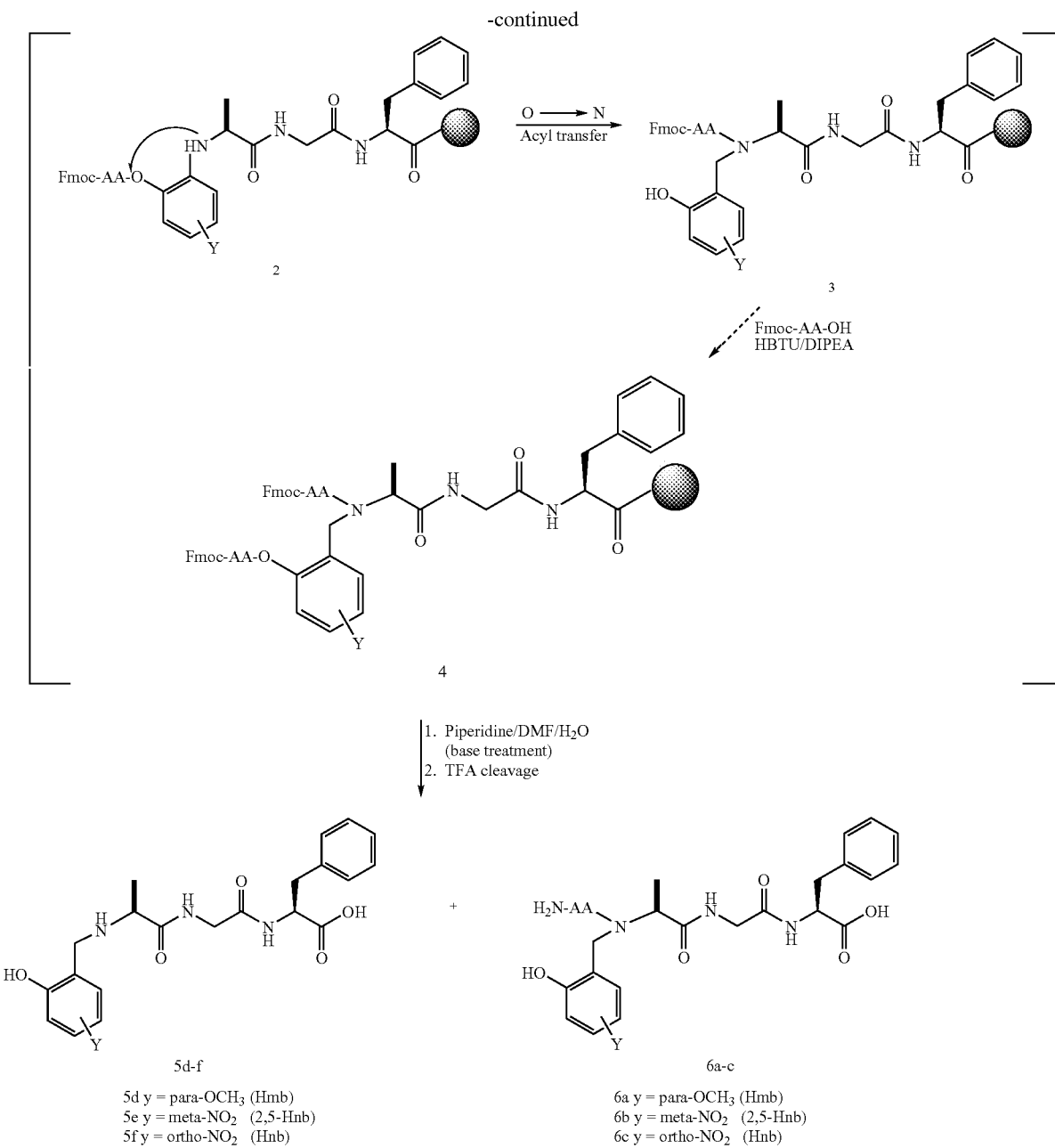

5d y = para-OCH₃ (Hmb)
5e y = meta-NO₂ (2,5-Hnb)
5f y = ortho-NO₂ (Hnb)

6a y = para-OCH₃ (Hmb)
6b y = meta-NO₂ (2,5-Hnb)
6c y = ortho-NO₂ (Hnb)

2,5-Hnb auxiliary (1b) was rapid for all three amino acids. For alanine and phenylalanine, $N^\alpha$-acylation products formed rapidly, and the reaction was near completion after 10 min. In a similar manner to the 2,5-Hnb auxiliary, high alanine, phenylalanine, and valine acyl transfer efficiencies were also observed with the Hnb auxiliary (1c) after 1 h. Importantly, for the more sterically demanding acylation of valine onto $N^\alpha$-(Aux)Ala-Gly-Phe the yields with both the 2,5-Hnb (>95%) and Hnb (88%) auxiliaries were nearly eight-times higher than with the Hmb auxiliary (12%) under identical experimental conditions. The position of the nitro-substituent on the aromatic ring of the auxiliary does not appear to play a crucial role. In all cases racemisation from the acyl transfer reaction was not evident.

TABLE 2

Distribution of $N^\alpha$-acylation products on the Ala-Gly-Phe sequence by $N^\alpha$-auxiliary directed O→N acyl migration.
$N^\alpha$-(Auxiliary) Ala-Gly-Phe $N^\alpha$-Acylation Yield (%)

| Auxiliary | t (min) | Alanine | Phenylalanine | Valine |
|---|---|---|---|---|
| 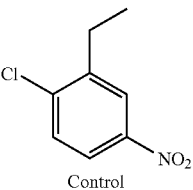 Control | 30 | <1 | <1 | <1 |

TABLE 2-continued

Distribution of N$^\alpha$-acylation products on the Ala-Gly-Phe sequence by N$^\alpha$-auxiliary directed O→N acyl migration.
N$^\alpha$-(Auxiliary) Ala-Gly-Phe N$^\alpha$-Acylation Yield (%)

| Auxiliary | t (min) | Alanine | Phenylalanine | Valine |
|---|---|---|---|---|
| HMB | 1 | 52 | 39 | 9 |
|  | 10 | 53 | 42 | 10 |
|  | 60 | 92 | 48 | 12 |
| 2,5-HnB | 1 | 74 | 42 | 27 |
|  | 10 | 92 | 79 | 60 |
|  | 60 | 97 | 85 | 95 |
| 2,6-HnB | 1 | 80 | 88 | 35 |
|  | 10 | 93 | 93 | 65 |
|  | 60 | 97 | 93 | 88 |

To determine if the activating effect of the nitro substituent could also improve acyl transfer rates and yields with more sterically demanding residues a second set of acylation experiments were carried out. In these experiments, the same auxiliaries were each introduced onto the resin-bound tetrapeptide, Val-Ala-Gly-Phe (SEQ ID NO:9), by reductive alkylation and subjected to acylation by HBTU-activated Fmoc-Gly, Fmoc-Phe and Fmoc-Val. Due to the inherent difficulty associated with the acylation of sterically hindered secondary amines the acyl transfer reaction time course in these experiments was increased to 1, 6, and 24 h. Following acylation, the peptide-resins were subjected to piperidine base treatment to exclusively observe the N$^\alpha$-amino acylation products and then cleaved with 0.5% TFA in DCM for 30 min. The products were identified by ES-MS or LC/MS analysis and quantified by RP-HPLC peak integration. The results are summarised in Table 3.

TABLE 3

Distribution of N$^\alpha$-acylation products on the Val-Ala-Gly-Phe (SEQ ID NO: 9) sequence by N$^\alpha$-auxiliary directed O→N acyl migration.
N$^\alpha$-(Auxiliary) Val—Ala-Gly-Phe N$^\alpha$-Acylation Yield (%)

| Auxiliary | t (h) | Glycine | Phenylalanine | Valine |
|---|---|---|---|---|
| HMB | 1 | 65 | 4 | ND* |
|  | 6 | 72 | 17 | <1 |
|  | 24 | 77 | 54 | 23 |
| 2,5-HnB | 1 | >98 | 37 | 11 |
|  | 6 | >99 | 91 | 42 |
|  | 24 | >99 | 97 | 95 |
| 2,6-HnB | 1 | 66 | 38 | 31 |
|  | 6 | 87 | 86 | 75 |
|  | 24 | 94 | 94 | 93 |

*ND indicates N$^\alpha$-acylation product not detected.

Distribution of N$^\alpha$-acylation products on the Val-Ala-Gly-Phe (SEQ ID NO:9) sequence by N$^\alpha$-auxiliary directed O→N acyl migration. From the acylation results listed in Table 3, it is clear that the nitro-activated auxiliaries strongly enhance O→N acyl transfer rates and yields with respect to the Hmb auxiliary. In all three cases the 2,5-Hnb auxiliary and Hnb were superior acyl transfer auxiliaries. The 2,5-Hnb-assisted acyl transfer of glycine onto valine proceeded rapidly, and was essentially complete (>98%) within 1 h, whereas phenylalanine and valine required 24 h for greater than 95% completion. The Hnb auxiliary also induced rapid acyl transfer, but nevertheless still required 24 h for approximately 95% N$^\alpha$-acylation for all three amino acids. On the other hand, Hmb-assisted acyl transfer resulted in unacceptably low N$^\alpha$-acylation yields, especially with phenylalanine and valine, even though O-acylation proceeds in approximately 50% and 90% yield after 1 h, respectively. More specifically, the Hmb-assisted N$^\alpha$-acylation of valine only proceeds in 23% yield after 24 h, and is approximately four times lower than with either the 2,5-Hnb (95%) or Hnb (93%) auxiliary. These results strongly indicated that the 2,5-Hnb and Hnb auxiliaries are of considerable value for the chain assembly of "difficult" peptide sequences, especially when β-branched or bulky residues are predominant.

Experimental

Peptide Synthesis. Peptides were chemically synthesised stepwise, using 0.5 M HBTU-DMF activation protocols for Fmoc and Boc chemistry as previously described. The syntheses were performed on p-benzyloxybenzyl alcohol (Wang) resin or chlorotrityl resins. The following amino acid side chain protection was used: Fmoc-Glu(O-tert-butyl)-OH, Fmoc-Lys-(Boc)-OH, Fmoc-Ser(O-benzyl)-OH, Fmoc-Thr(O-tert-butyl)-OH, and Fmoc-Tyr(O-tert-butyl)-OH. Each residue was coupled for 10 min, and coupling efficiencies determined by the quantitative ninhydrin reaction and the qualitative isatin test.

Reductive Alkylation. Typical procedure for the incorporation of the auxiliaries onto a growing peptide chain during SPPS. 0.1 mmole of the $N^\alpha$-deprotected peptide-resin was washed with 10 mL DMF/MeOH/AcOH (9:9:2), drained, and then mixed with 3 equiv of the substituted benzaldehyde in 1 mL of DMF/MeOH (1:1) for 30 min. The solution was then drained and imine formation reaction repeated. Following drainage, the resin was washed briefly with DMF, then 5 equiv of sodium borohydride in DMF/MeOH/AcOH (9:9:2) was added and mixed at room temperature for 5 min. The resin was then drained and washed successively with DMF, DMF/$H_2O$, $H_2O$, MeOH/DCM, DCM, and DMF. A few milligrams (~3 mg) was then taken, dried, cleaved with 97% aqueous TFA, dissolved in 30% buffer B, filtered, and then immediately analyzed by ES-MS and RP-HPLC to determine reaction completion.

Acylation Experiments. The Ala-Gly-Phe and Val-Ala-Gly-Phe (SEQ ID NO:9) sequences were assembled on chlorotrityl resin (0.96 mmol/g, PepChem) using standard Fmoc/HBTU protocols. The resin was then divided into three portions in separate reaction vessels, and swollen in DMF for 10 min. Three equiv of Fmoc-protected glycine, alanine, phenylalanine, and valine were coupled to Ala-Gly-Phe-resin or Val-Ala-Gly-Phe-resin (SEQ ID NO:37) using 2.95 equiv of 0.5 M HBTU in DMF with 4 equiv of DIEA for 1, 10, and 60 min or 1, 6, and 24 h, respectively. To examine $N^\alpha$-acylation exclusively and also remove Fmoc groups, resins samples before cleavage were subjected to 2 cycles of 5 min piperidine/DMF (1:1) and 5 min DMF/piperidine/$H_2O$ (4:4:2) treatments, then dried with DCM:MeOH (1:1). Trityl resin samples were cleaved with 0.5% TFA in DCM for 30 min. The TFA cleavage solutions were evaporated with a stream of nitrogen, and the product dissolved in 100 µL of 50% buffer B. Samples were centrifuged, supernatant collected, then immediately analysed by RP-HPLC and ES-MS or LC/MS.

Example 8

Synthesis of a 'Difficult' Peptide, STAT-91 (699-709)

In principle, the 2,6-Hnb and Hmb groups should have a similar effect on disrupting hydrogen-bonding networks, since they both alter the backbone structure of growing peptide chains and remove a backbone hydrogen-bond donor. To demonstrate this beneficial effect, the STAT-91(699-709) sequence, TGYIKTELISV (SEQ ID NO:38), which we have previously reported as "difficult" in both Fmoc- and Boc-SPPS (Meutermans et al 1996; Alewood et al, 1997), was assembled using standard chain assembly protocols and also with the assistance of N-Hnb backbone substitution under identical experimental conditions. The STAT-91 peptide was selected because it does not contain a relatively unhindered site before the "difficult" section is encountered, and thus precludes the use of the Hmb auxiliary.

Using standard Fmoc/tent-butyl 0.5 M HBTU/DIEA 10 min coupling protocols in DMF, the chain assembly of STAT-91 (699-709) proceeds well until residues $Glu^{705}$ and $Thr^{704}$ which only couple in 67% and 91% yield, respectively. This is then followed by a 59% coupling yield at $Lys^{703}$, which reportedly only increases to 62% upon re-coupling after 1 h. Furthermore, substitution of HBTU with HATU did not significantly improve the coupling yield for this residue. $Tyrosine^{700}$ also gave a poor coupling yield (61%) that also does not improve significantly even after re-coupling for 1 h. In short, the chain-assembly of STAT-91(699-709) under standard coupling conditions proceeded with an unacceptable average acylation yield of 83% (see figure below). However, when the Hnb (3) auxiliary is incorporated onto the backbone of the growing peptide at $Ile^{707}$ (the third residue from the resin-linker) by reductive alkylation, subsequent chain-assembly proceeded in high efficiency using the same coupling conditions. With the assistance of the Hnb auxiliary, the average coupling yield for the assembly of $Ile^{707}(N^\alpha$-Hnb)-STAT-91(699-709) increased to 99.6% as determined by the quantitative ninhydrin assay. This is illustrated in FIG. 1.

The HBTU-mediated $N^\alpha$-acylation of $Leu^{706}$ onto the $N^\alpha$-Hnb-substituted $Ile^{707}$ was monitored by ES-MS and RP-HPLC analysis of a cleaved resin sample before continuation. The Fmoc-Leu to $N^\alpha$-(Hnb)Ile-Ser-Val-resin acyl transfer reaction was approximately 50% complete after 1 h, but apparently quantitative after 24 h as determined by RP-HPLC analysis (data not shown). By comparison, for the identical Fmoc-Leu to $N^\alpha$-(Hmb)Ile-Ser-Val-resin acyl transfer reaction, $N^\alpha$-acylation only proceeds in 21% yield after the same period. This poor Hmb-assisted $N^\alpha$-acylation yield further highlights the limitation of the Hmb auxiliary in the synthesis of hindered or β-branched containing "difficult" peptides.

Following chain-assemblies, the crude TFA cleavage material of the standard and Hnb-assisted STAT-91(699-709) syntheses were analysed by ES-MS and RP-HPLC. When employing standard Fmoc/HBTU synthesis protocols, no appreciable amount (<1%) of the target STAT-91 peptide was found in the crude product by either ES-MS or RP-HPLC analysis. In contrast, with the Hnb-assisted synthesis, the Hnb-substituted STAT-91(699-709) peptide was the major component in the crude cleavage material as determined by ES-MS and RP-HPLC. The $Ile^{707}(N^\alpha$-Hnb)-STAT-91(699-709) peptide was then readily photolysed at 366 nm for 3 h to give the target peptide in good yield. From this comparison, it appears that the Hnb auxiliary can be used to significantly improve the chain-assembly efficiencies of "difficult" peptides in a manner similar to that of Hmb-substitution, but with the key advantage of greatly improved acyl transfer efficiency.

Experimental

STAT-91(699-709) Syntheses The standard and Hnb-assisted synthesis of STAT-91(699-709) was carried out using Fmoc chemistry on Fmoc-Val-Wang resin (Applied Biosystems Inc., 0.70 mmol/g, 0.1 mmole synthesis scale). The standard assembly using 10 min couplings times resulted in an average coupling yield of 83%. The Hnb-assisted Fmoc chain-assembly of STAT-91(699-709) was also performed using 10 min coupling times, with an average coupling yield of 99.6%. The Hnb auxiliary was introduced at $Ile^{707}$ by reductive amination (2×3 h imine formation reaction using 5 equiv Hnb) and was then followed by the 0.5 M HBTU coupling of $Leu^{706}$ in DMF. $N^\alpha$-acylation of $Leu^{706}$ onto $Ile^{707}(N^\alpha$-Hnb)-STAT-91 (708-709)-resin was complete after 24 h as determined by ES-MS and RP-HPLC analysis following TFA cleavage of small resin sample. To maintain experimental consistency, $Ile^{707}$ in the standard synthesis was also coupled with HBTU for 24 h. In both cases, the final peptide-resin product was cleaved with 97% aqueous TFA at room temperature for 1 h. After evaporation of the TFA in vacuo, the crude product was washed with cold diethyl ether (2×5 mL), dissolved in 30% B (5 mL), and lyophilised. Ile$^{707}$(N$^{\alpha}$-Hnb)-STAT-91(699-709) ES-MS: M$_r$ 1374.1 Da; calculated for C$_{63}$H$_{99}$N$_{13}$O$_{21}$: 1373.7 Da (monoisotopic); The Hnb-substituted STAT peptide was then photolysed as described below to give the target peptide in 76% yield after RP-HPLC purification: STAT-91(699-709) ES-MS: M$_r$ 1222.7 Da; calculated for C$_{56}$H$_{94}$N$_{12}$O$_{18}$: 1222.68 Da (monoisotopic).

Photolysis. Photolysis was carried out in a CAMAG UV-cabinet II, with a lamp wavelength of 366 nm and power of 0.25 Amps for 2-3 h. Typically 5 mg samples of peptide-resin or 1 mg samples of peptide were taken up in 500 µl, MeOH in an uncovered wide-mouth vial on a white mat.

Example 9

Synthesis of a difficult cyclic peptide, Ala-Phe-Leu-Pro-Ala (SEQ ID. NO:10)

H-Ala-Phe-Leu-Pro-Ala-OH (SEQ ID NO:39) was a recently reported example of a sequence which is difficult to cyclise (Schmidt and Langner, 1997). When subjected to cyclisation conditions, dimer and higher oligmers were generated, but no target cyclopentapeptide was formed. We have employed this linear peptide to probe our methodology and compare it with the prior art methods. In the following set of experiments we demonstrate that this Ala-Ala amide bond in the monocycle was not accessible from this linear peptide using prior art methodologies, but was accessible using our photolabile auxiliaries.

Cyclisation of Unsubstituted Ala-Phe-Leu-Pro-Ala (SEQ Id NO:19).

As a control experiment we attempted to cyclise the unsubstituted linear peptide (Ala-Phe-Leu-Pro-Ala) (SEQ ID NO:19) using standard cyclisation conditions (1 mM in DMF, 3 eq. BOP, 5 eq. DIEA, 3 h at rt). As expected from the previously reported results, only cyclic dimer and some trimer were obtained, but no target monocyclic product.

Cyclisation Using Ethanethiol Auxiliary

We initially evaluated an ethanethiol auxiliary. This auxiliary was introduced via an on-resin Fukuyama synthesis as described in Example 3, using the reaction sequence summarized in Scheme 12, wherein Ala-Phe-Leu-Pro-Ala is SEQ ID NO:19.

Scheme 12 Cyclisation of the N-mercaptoethanyl peptide 1: i) 3 eg. BOP/5 eq. DIEA, 3h at rt; ii) 0.1 M NH$_4$HCO$_3$.

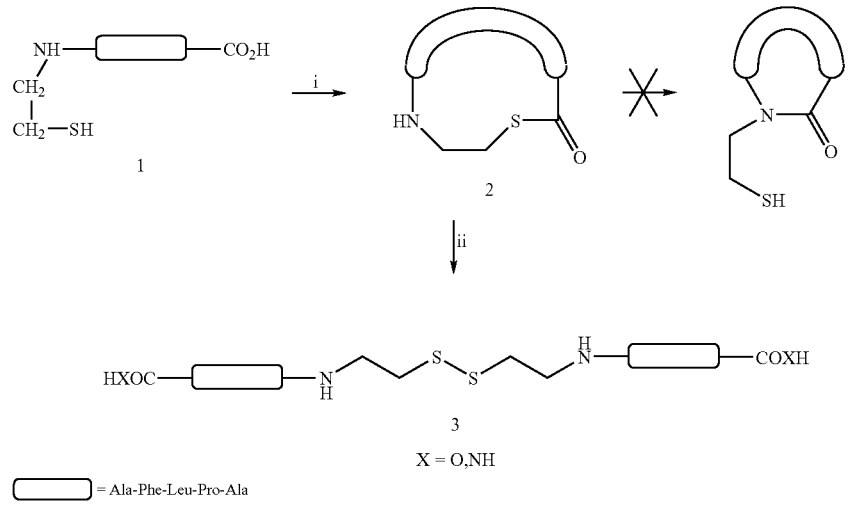

X = O,NH

☐ = Ala-Phe-Leu-Pro-Ala

Cyclisation of the N-ethanethiol derivative 1 yielded only the monocyclic product 2 (45% isolated yield), as determined by mass spectral analysis (correct molecular weight and isotope distribution). No dimeric or other oligomeric products were found in the crude reaction mixture.

The monocyclic product has the thioester structure, as confirmed by saponification of the monocyclic product 2 in NH$_4$HCO$_3$ which generated disulfides 3 of the linear peptide amides and acids. Attempts to force ring contraction by heating (65° C.) the isolated ester in organic solvents (DMF, dioxane) in the presence of base (DIEA, DBU), or heating in aqueous buffers (pH 4-8) failed. The ester either remained unchanged or hydrolysed to the linear peptide.

This failure to ring contract is in our view due to the low reactivity of the alkylthioester towards secondary amines rather than a constrained transition state geometry. We decided to examine the 2-hydroxynitrobenzaldehydes in a ring contraction approach, as initial cyclisation would generate a more reactive nitrophenylester with significantly improved acyl transfer kinetics.

Cyclisation Using 5-Nitro-2-Hydroxybenzyl Auxiliary.

The peptide 4a was synthesised as described in Example 4. Cyclisation of peptide 4a under standard conditions initially yielded two monocyclic products, as well as significant amounts of a side product 6a (Mr, 812 Da), caused by reaction of the phenol functionality with excess BOP in the reaction mixture (Scheme 13, A). By adjusting the amount of activating reagent and base, formation of this side product was completely avoided. The reaction conditions were further optimised by altering the temperature and amount of base after an initial cyclisation period and monitoring the formation of monocyclic products by LC/MS analysis. The best results were obtained when after 3 h of reaction (1 mM in DMF, leg BOP, 2 eq DIEA, rt) excess DIEA (10 eq) was added and the mixture left standing for 24 h or heated to 65° C. for 1 hour.

In an attempt to isolate the intermediate cyclic ester 8a, the reaction mixture was analysed after the initial 3 h cyclisation period by HPLC (FIG. 2A) and LC/MS. The mixture contained linear peptide and monocyclic products 10a and 10b,

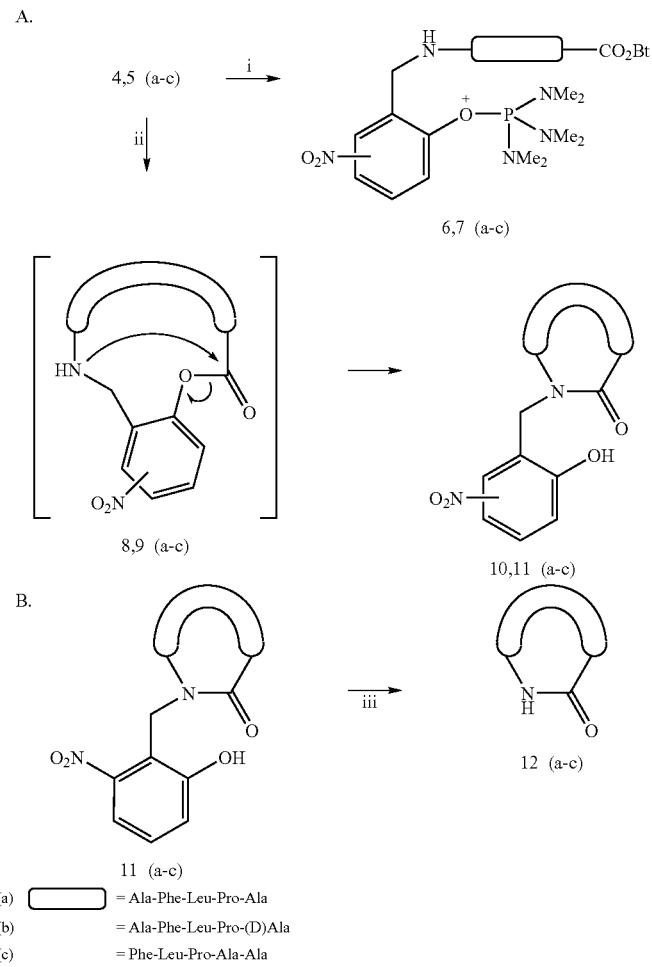

Scheme 13: Cyclisation of auxiliary containing peptides 4,5 (A) and formation of the target cyclic peptides 10,11 (B); i) 3 eq. BOP/5 eq. DIEA, 3 h at rt; ii) 1 eq. BOP/2 eq. DIEA, 3 h rt; 10 eq. DIEA, 12 h rt or 1 h at 65° C.; iii) hv (366 nm), wherein Ala-Phe-Leu-Pro-Ala is SEQ ID NO:19 and Phe-Leu-Pro-Ala-Ala is SEQ ID NO:31.

The HPLC profile of the crude product is depicted in FIG. 2B. The main product (50% isolated yield) was unambiguously characterised by NMR, ES-MS and chiral amino acid analysis as the all-L target monocyclic product 10a. A $^1$H NMR absorption at 11.5 ppm confirmed that the product contained the free hydroxy substituent, and thus did not have the ester structure but rather the target cyclic amide structure. Further, a small amount of the C-terminally racemised product 10b was also isolated (see FIG. 2B). A chiral amino acid analysis of the product displayed the presence of a D-Ala residue.

but no monocyclic ester was found. The p-nitrophenyl ester presumably hydrolyses in the aqueous work-up to the linear peptide.

Cyclisation Using 6-Nitro-2-Hydroxybenzyl Auxiliary.

As the 5-nitro-2-hydroxybenzyl auxiliary is not readily removed after cyclisation, we examined the 6-nitro-2-hydroxybenzyl auxiliary peptide 5a towards cyclisation. The ortho-nitro substituent, while maintaining a similar activation effect on the ring contraction of the cyclic intermediate 9a compared to 8a, has the added benefit that it should render the auxiliary photolabile. The linear peptide 5a was synthesised and treated as described above for the 5-nitro-2-hydroxy derivative. Thus cyclisation (at 1 mM in DMF, 1 eq. BOP/2 eq. DIEA) was performed at rt for 3 h, followed by addition of excess DIEA (10 eq) and heating to 65° C. for 1 hour. The major product was isolated in 39% yield, and characterised by NMR and chiral amino acid analysis as the all-L cyclo-pentapeptide 11a. A small amount of the C-terminal racemised cyclic product 11b (containing a D-Ala) was also isolated.

Similarly N-(6-nitro-2-hydroxybenzyl)Phe-Leu-Pro-Ala-Ala (SEQ ID NO:11) 5c was assembled and cyclised as above. The all-L cyclo pentapeptide 11c was isolated in 45% yield.

Figure 3:
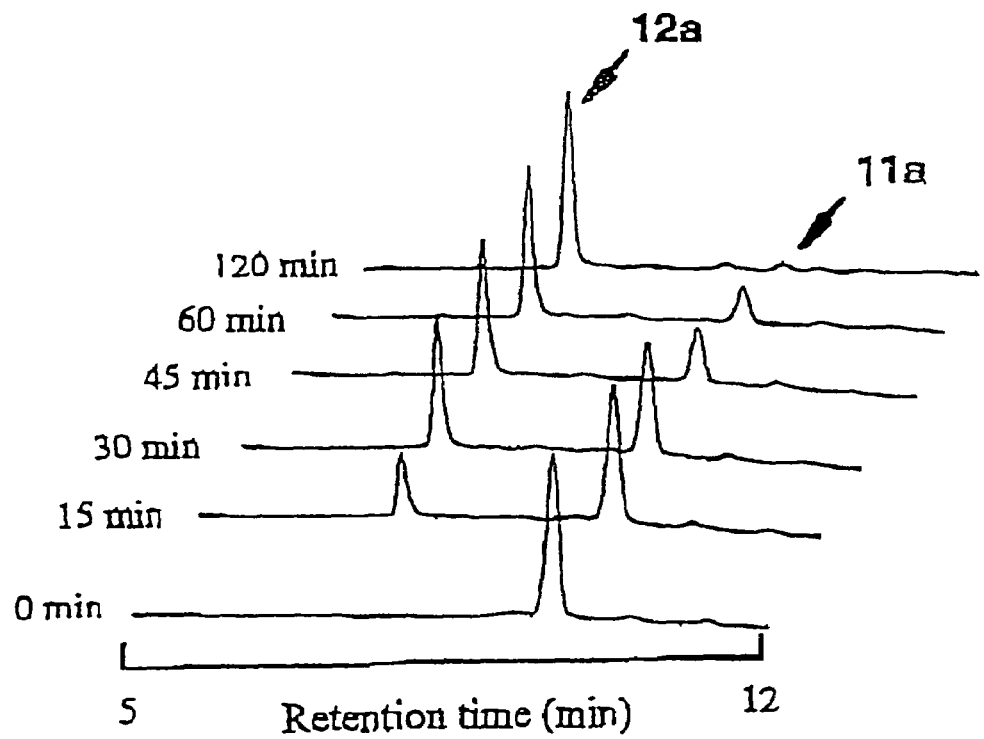
FIG. 3 shows the results of HPLC analysis of the photolysis of cyclic peptide 11a at timed intervals. A 0.15 mM solution of peptide 11a in MeOH/1% AcOH was photolysed using a standard UV lamp and at different time intervals small aliquots were injected onto a Zorbax reversed-phase C-18 (3 μm, 300 Å, 0.21×5 cm) HPLC column. The products were separated using a linear 0-80% buffer B gradient over 10 min at a flow rate of 200 μL/min (detection at 214 nm).

Removal of the auxiliary. Cyclic peptide 11a was then subjected to photolysis at 366 nm, using a standard UV lamp, in a range of solvent conditions. In most solvents (MeOH, MeOH/AcOH, THF/AcOH, dioxane) the nitrobenzyl substituent on the backbone nitrogen is readily removed to generate the target cyclic peptide 12a (Scheme 14, B). FIG. 3 illustrates the clean and efficient conversion (11a to 12a).

The cyclic product was characterised by chiral amino acid analysis and $^1$H NMR. The spectral data were in good agreement with the reported data. Furthermore, an independent sample of cyclic peptide, prepared from the cyclisation of Phe-Leu-Pro-Ala-Ala (SEQ ID NO:31) according to Schmidt et al (1997) coeluted with the product obtained from photolysis.

The same product 12a was obtained from photolysis of the regio analogue 11c. The racemised cyclic product 11b was photolysed, and similarly produced the unsubstituted D-Ala containing product 12b, which coeluted with an independently synthesised sample.

Experimental

Cyclisation experiments. Cyclisation of auxiliary-containing peptides 4 and 5: 1 equivalent of BOP and 2 equivalents of DIEA in DMF were added to a 1 mM solution of the linear peptide in DMF and stirred for 3 h at rt. 10 equivalents of DIEA was then added and the solution heated at 65° for 1 h. DMF was removed in vacuo and the crude product dissolved in acetonitrile/water (1:1) and purified by RP-HPLC.

Cyclisation of other linear peptides: Cyclisations were performed using a 1 mM solution of linear peptide in DMF. 3 equivalents of BOP and 5 equivalents of DIEA were added and the solution stirred for 3 h at rt. Work-up was as described above.

Cyclo-[S—(CH$_2$)$_2$-Ala-Phe-Leu-Pro-Ala] (SEQ ID NO:12) 2. Cyclisation of HS—(CH$_2$)$_2$-Ala-Phe-Leu-Pro-Ala (SEQ ID NO:13) 1 (10 mg of the TFA salt, 0.014 mmol) produced the monocyclic thioester 2 (3.4 mg, 45% yield): Mr: 559.3, calcd for $C_{28}H_{41}N_5O_5S$: 559.3. The thioester was hydrolysed using aqueous ammonium bicarbonate buffer (0.1 M, pH 8, 6 h at 60° C.) to form the C-terminal amides and acids. Under the mild base conditions these thiol-products oxidised to the disulfides 3 which were characterised by ES-MS. [S—(CH$_2$)$_2$—NH—CH(CH$_3$)—CO-Phe-Leu-Pro-Ala-NH$_2$]$_2$ (SEQ ID NO:40) Mr: 1150.8, calcd for $C_{56}H_{86}N_{12}O_{10}S_2$: 1150.6, [S—(CH$_2$)$_2$—NH—CH(CH$_3$)—CO-Phe-Leu-Pro-Ala-NH$_2$]—S—(CH$_2$)$_2$—NH—CH(CH$_3$)—CO-Phe-Leu-Pro-Ala-OH (SEQ ID NO:14) Mr: 1151.8, calcd for $C_{56}H_{85}N_{11}O_{11}S_2$: 1151.6, [S—(CH$_2$)$_2$—NH—CH(CH$_3$)—CO-Phe-Leu-Pro-Ala-OH]$_2$ (SEQ ID NO:41) Mr: 1152.8, calcd for $C_{56}H_{84}N_{10}O_{12}S_2$: 1152.6.

Cyclo-[N-(5-nitro-2-hydroxybenzyl)-Ala-Phe-Leu-Pro-Ala] (SEQ ID NO:42) (10a). Cyclisation of N-(5-nitro-2-hydroxybenzyl)-Ala-Phe-Leu-Pro-Ala (SEQ ID NO:15) 4a (30 mg of the TFA salt, 0.038 mmol), produced 10a (12.5 mg, 0.019 mmol) in 51% yield: ES-MS Mr 650.2, calcd for $C_{33}H_{42}N_6O_8$: 650.3 (monoisotopic). $^1$H NMR (500 MHz, DMSO-d$_6$, ppm) δ 11.5 (s, 1H, OH), 8.40 (d, 1H, NH$_{Leu}$), 8.02 (dxd, 1H, H-ar), 7.70 (d, 1H, H-ar), 7.4 (d, 1H, HN$_{Phe}$), 7.20-7.30 (m, 5H, H-Phe), 6.99 (d, 1H, H-ar), 6.54 (d, 1H, H—N$_{Ala}$), 5.00 (s, 1H, ArCHhN—), 4.91 (m, 1H, α-Ala$^5$), 4.75 (q, 1H, α-Ala$^1$), 4.59 (m, 1H, α-Phe), 4.50 (m, 1H, α-Leu), 4.27 (t, 1H, α-Pro), 3.88 (d, 1H, ArCHhN—), 3.62 (m, 1H, δ-Pro), 3.37 (m, 1H, δ-Pro), 2.97 (m, 1H, β-Phe), 2.82 (m, 1H, β-Phe), 2.04 (m, 2H, β-Pro), 1.88 (m, 1H, γ-Pro), 1.73 (m, 1H, β-Leu), 1.65 (m, 1H, γ-Pro), 1.44 (m, 1H, γ-Leu), 1.33 (m, 1H, β-Leu), 1.24 (d, 3H, β-Ala$^5$), 0.91 (d, 3H, β-Ala$^1$), 0.85 (m, 6H, δ-Leu). $^{13}$C NMR (75 MHz, DMSO-d$_6$, ppm) δ 172.61, 170.34, 170.07, 169.95, 169.47, 160.40, 139.73, 136.88, 129.31, 128.14, 126.50, 125.72, 124.21, 122.65, 115.00, 61.04, 56.50, 55.74, 48.70, 46.31, 44.34, 41.37, 38.28, 31.30, 24.20, 22.81, 22.68, 21.17, 18.97, 15.35.

Cyclo-[N-(6-nitro-2-hydroxybenzyl)-Ala-Phe-Leu-Pro-Ala] (SEQ ID NO:16) (11a). From cyclisation of N-(6-nitro-2-hydroxybenzyl)-Ala-Phe-Leu-Pro-Ala (SEQ ID NO:43) 5a (20 mg of the TFA salt, 0.025 mmol), 11a (6.5 mg, 0.010 mmol) was obtained in 39% yield: ES-MS Mr 650.6, calcd for $C_{33}H_{42}N_6O_8$: 650.3 (monoisotopic). $^{13}$C NMR (75MHz, CD$_3$OD, ppm) δ 178.07, 176.95, 174.54, 174.32, 173.72, 159.11, 153.19, 140.41, 131.99, 129.96, 129.54, 127.57, 121.18, 116.57, 62.75, 60.67, 58.55, 54.05, 51.15, 44.54, 43.41, 34.85, 33.67, 25.03, 24.13, 22.30, 21.31, 15.49, 13.89.

Cyclo-[N-(6-nitro-2-hydroxybenzyl)-Phe-Leu-Pro-Ala-Ala] (SEQ ID NO:17) (11c). From cyclisation of the N-(6-nitro-2-hydroxybenzyl)-Phe-Leu-Pro-Ala-Ala (SEQ ID NO:18) (20 mg of the TFA salt, 0.025 mmol), 11a (7.3 mg, 0.011 mmol) was obtained in 44% yield: ES-MS Mr 650.2, calcd for $C_{33}H_{42}N_6O_8$: 650.3 (monoisotopic). $^{13}$C NMR (75 MHz, DMSO-d6, ppm) δ 171.43, 171.00, 169.46, 167.56, 156.65, 138.43, 129.24, 129.05, 128.32, 128.18, 126.08, 119.50, 115.87, 114.60, 62.18, 60.69, 51.07, 49.38, 46.57, 45.46, 41.54, 38.17, 33.65, 31.43, 24.37, 22.73, 22.32, 21.06, 17.87, 16.92.

Cyclo-[Ala-Phe-Leu-Pro-Ala] (SEQ ID NO:10) (12a). a) Cyclo-[N-(6-nitro-2-hydroxybenzyl)-Ala-Phe-Leu-Pro-Ala] (SEQ ID NO:16) (1 mM MeOH) was purged with nitrogen for 30 minutes and then photolysed with a standard laboratory UV lamp (366 nm, 0.25 A) for three hours. The MeOH was evaporated and residue dissolved in 50% buffer B and the solution loaded directly onto a Vydac C18 column (preparative) for HPLC purification. Cyclo-[Ala-Phe-Leu-Pro-Ala] (SEQ ID NO:10) was isolated in 52% yield. The product coeluted with a independently synthesised sample. ES-MS Mr 499.4, calcd for $C_{26}H_{37}N_5O_5$, 499.3 (monoisotopic).

b) Photolysis of purified cyclo-[N-(6-nitro-2-hydroxybenzyl)-Phe-Leu-Pro-Ala-Ala] (SEQ ID NO:17) was performed as described above. Cyclo-[Phe-Leu-Pro-Ala-Ala] (SEQ ID NO:20) was isolated in 28% yield. The product coeluted with a independently synthesised sample. ES-MS Mr 499.1, calcd for $C_{26}H_{37}N_5O_5$, 499.3 (monoisotopic).

Example 10

Application of the Photolabile Auxiliary for the Cyclisation of an all-L-Tetrapeptide, Tyr-Arg-Phe-Gly (SEQ ID NO:21), Via a Ring Contraction Approach We decided to investigate the feasibility of our auxiliary approach for the synthesis of a more constrained all-L cyclo tetrapeptide. Standard cyclisation of the linear peptide Tyr-Arg-Phe-Gly (SEQ ID NO:21) yields cyclic monomer/cyclic dimer/cyclic trimer in a ratio of 2/8/3. Cyclisation of (HnB) Tyr-Arg-Phe-Gly (SEQ ID NO:22) was performed as described before, but heating (65° C. after DIEA addition)

was continued for 20 hours (instead of 1 h). The product cyclo-[(HnB)Tyr-Arg Phe-Gly] (SEQ ID NO:23) was isolated in 40% yield. Photolysis of this product in MeOH/AcOH was slow and yielded impure cyclo[Tyr-Arg-Phe-Gly] (SEQ ID NO:24), whereas photolysis in THF, DMF or Dioxane was significantly faster (complete in hour). The cyclo-[Tyr-Arg-Phe-Gly] (SEQ ID NO:24) was isolated in 41% yield (photol. step).

Example 11

Native Ligation

In this experiment we illustrate how we bring this auxiliary approach into practice for performing native ligation. Two ligation sites were examined, ie. a non-hindered site, Gly-Gly, and a more hindered site, Phe-Ala. The oxyethanethiol auxiliary approach has been applied to these ligation sites (Canne et al, 1996), and was only successful in the first, non-hindered, case.

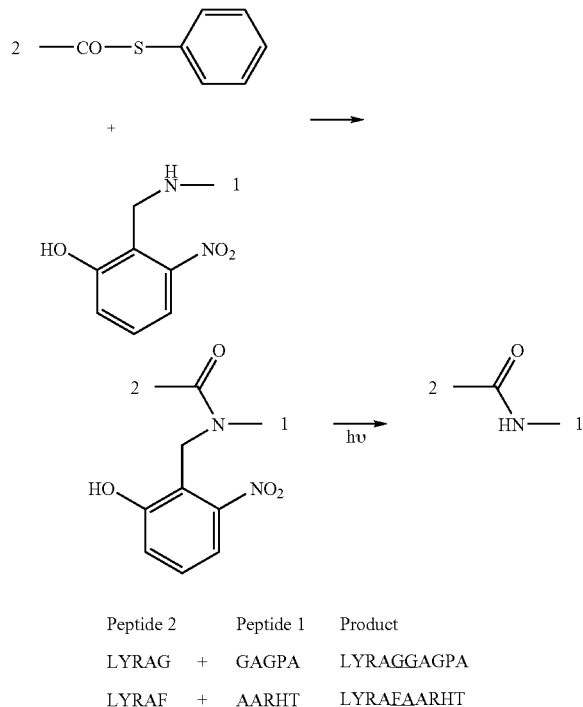

| Peptide 2 | Peptide 1 | Product |
|-----------|-----------|---------|
| LYRAG + | GAGPA | LYRAGGAGPA |
| LYRAF + | AARHT | LYRAFAARHT |

The first peptide segments (peptide 1; GAGPA is SEQ ID NO:26 and AARHT is SEQ ID NO:29) are assembled using standard in situ neutralisation protocols and the auxiliary is introduced as described in Examples 1 to 5. Standard HF cleavage and side chain deprotection provides the first unprotected peptide segment. The second peptide segments (peptide 2; LYRAG is SEQ ID NO:25 and LYRAF is SEQ ID NO:28), containing a thiophenylester at the C-terminus, are synthesised as described before (Canne et al, 1996).

To optimise the ligation conditions the following experiments are then performed: peptide 1 and peptide 2 are dissolved in DMF at 1 mM, 10 mM and 100 mM concentration and 2 or 5 equivalents of DIEA added. Progress of the reaction is monitored for each experiment by HPLC and LCMS analysis at different time intervals. Several other solvent systems are tested, such as DMSO/DIEA, and aqueous buffers (pH ranging from 4 to 8) (no DIEA). The products are LYRAGGAGPA (SEQ ID NO:27) and LYRAFAARHT (SEQ ID NO:30).

Example 12

Backbone Linker

In this experiment we illustrate how we accommodate photolabile backbone linking using this auxiliary approach for the solid phase synthesis of cyclic peptides. Cyclo-FLPAA is SEQ ID NO:20.

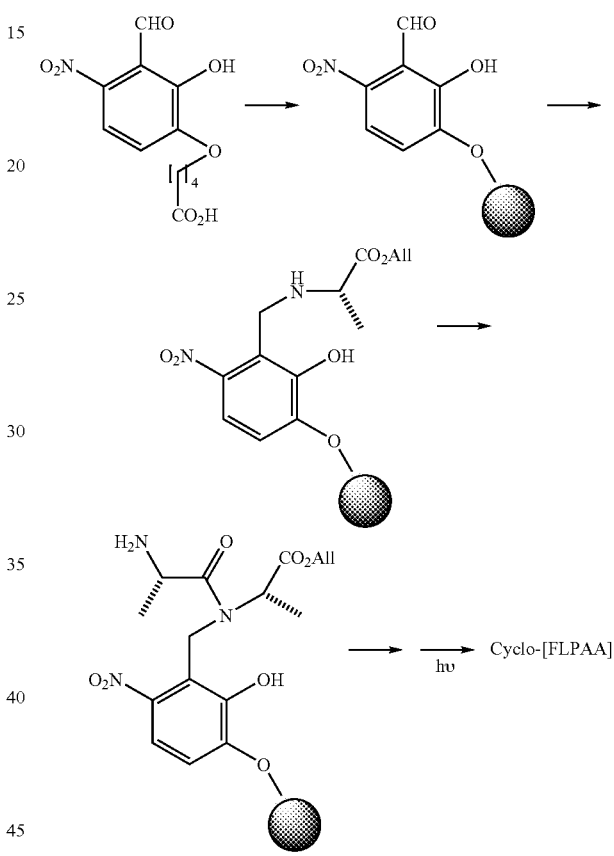

2,3-dihydroxy-6-nitrobenzaldehyde (Perez et, al, 1992) is treated with 1 equivalent bromovaleric acid and 1 equivalent $KHCO_3$ in acetone. The resulting acid is linked to aminomethylated polystyrene. Alanine allyl ester is attached to the resin by reductive amination and the resulting secondary amine acylated with Boc-Ala-OH as described in Example 6. The linear peptide (Phe-leu-Pro-Ala-Ala) (SEQ ID NO:31) is further assembled using in situ neutralisation protocols. The N-terminus is deprotected with TFA and the C-terminal allyl protection group removed using $Pd[P(Ph)_3]_4$ as described. The cyclisation is then performed with BOP/DIEA in DMF and the product cleaved from the resin by photolysis.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Albericio, F. and Carpino, L. A. Methods in Enzymology, 1997 289 104-125

Alewood, P., Alewood, D., Miranda, L., Love, S., Meutermans, W. and Wilson, D. Methods in Enzymology, 1997 289, 14-29

Bitan, G., Muller, D., Kasher, R., Gluhov, E. and Gilon, C. J. Chem. Soc. Perkin Trans. 1, 1997 1501-1510.

Bodanszky, M. Principles of Peptide Synthesis, Springer-Verlag, Heidelberg (1984)

Botti, P., Pallin, T. and Tam, J. J. Am. Chem. Soc., 1996 118 10018-10024.

Camarero, J. A., Cotton, G. J., Adeva, A. and Muir, T. W. Int. J. of Pept. and Protein Res., 1998 51 303-316.

Camarero, J. A. and Muir, T. W. Chem. Comm., 1997 1369-1370.

Canne, L. E., Bark, S. J. and Kent, S. B. H. J. Am. Chem. Soc., 1996 118 5891-5896.

Cavalier-Frontin, F., Achmad, S., Verducci, J., Jacquier, R. and Pèpe, G. J. Mol. Struct. (Theochem), 1993 286 125-130.

Dawson, P. E., Muir, T. W., Clarklewis, I., and Kent, S. B. H. Science, 1994 266 776-779.

Ehrlich, A., Heyne, H. U., Winter, R., Beyermann, M., Haber, H., Carpino, L. A. and Bienert, M. J. Org. Chem., 1996 61 8831-8838.

Fotouhi, N., Galakatos, G., and Kemp, S. J. Org. Chem., 1989 54 2803-2817.

Freidinger, R. M., Perlow, D. S, and Veber, D. F. J. Org. Chem., 1982 59 104-109.

Fries, K. and Brothuhn, G. Chemische Ber., 1923 56 1630.

Goodlett, D. R.; Abuaf, P. A.; Savage, P. A.; Kowalski, K. A.; Mukherjee, T. K.; Tolan, J. W.; Goldstein, G.; Crowther, J. B. J. Chromatography A, 1995, 707, 233-244.

Hackeng, T. M., Mounier, C. M., Bon, C., Dawson, P. E., Griffin, J. H. and Kent, S. B. H. Proc. Natl. Acad. Sci. USA, 1997 94 7845-7850.

Harayama, T., Nakatsuka, K., Nishioka, H., Murakami, K., Ohmori, Y., Takeuchi, Y., Ishii, H. and Kenmotsu, K. Heterocycles, 1994 38 2729-2738.

Holmes, C. J. Org. Chem., 1997 62 2370-2380.

Hyde, C., Johnson, T., Owen, D., Quibell, M., and Sheppard, R. Int. J. Peptide Protein Res., 1994 43 431-440.

Jensen, K., Alsina, J., Songster, M., Vagner, J., Albericio, F. and Barany, G. J. Am. Chem. Soc., 1998 120 5441-5452.

Kemp, D., Galakatos, N., Dranginis, S., Ashton, C., Fotouhi, N., and Curran, T. J. Org. Chem., 1986 51 3320-3324.

Kemp, D., Kerkman, D., Leung, S, and Hanson, G. J. Org. Chem., 1981 46 490-498.

March, J. Advanced Organic Chemistry; 1985 17, 238

Meldal, M. Methods in Enzymology, 1997 289 83-104.

Meutermans W. D. F., Alewood, P. F. Tetrahedron Letters 1996 37 4765-4766

Nicolas, E., Pujades, M., Bacardit, J., Giralt, E. and Albericio, F. Tetrahedron Lett., 1997 38 2317-2320.

Perez, R., Fernandez-Alvarez, E., Nieto, O. and Piedrafita, F. J. Med. Chem., 1992 35 4584-4588.

Schmidt, U. and Langner, J. J. Pept. Res., 1997 49 67-73.

Shao, Y., Lu, W. and Kent, S. Tetrahedron Lett., 1998 39 3911-3914.

---

The invention claimed is:

1. A method of
   a) synthesis of a linear or cyclic peptide;
   b) synthesis of a C-terminal modified peptide; or
   c) on-resin cyclization of a peptide molecule,
   said method comprising at least the step of linking a cyclic aromatic auxiliary compound of General Formula II to a primary amine nitrogen atom of an amino acid, or of a peptide which is to be cyclized or modified, to form a secondary amine,

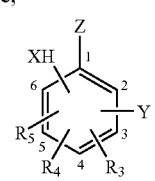

II in which
- XH is OH, SH, CH₂OH, or CH₂SH at position 2 or 3;
- Y is an electron-withdrawing group at position 5 or 6;
- Z is any group which allows the formation of a covalent carbon-nitrogen bond; and
- $R^3$, $R^4$ and $R^5$ are each independently selected from the group consisting of hydrogen, alkyl, aryl, hydroxy, alkoxy, aryloxy and a covalent linkage to a solid support; and
- in which $R^3$ and $R^4$, or $R^4$ and $R^5$ can optionally together with the ring form a 5-, 6-, or 7-membered ring, thereby to facilitate conversion of the secondary amine to an amide, activating the carboxylic acid group of the amino acid, or of a peptide which is to be cyclized or modified, and converting the secondary amine to an amide.

2. The method of claim 1, in which the XH group is at position 2.

3. The method of claim 1, in which Y is at position 6.

4. The method of claim 3, in which Y is $NO_2$.

5. The method of claim 1, in which the auxiliary compound is

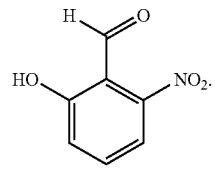

6. The method of claim 1, for synthesis of a cyclic peptide, a large peptide, or a difficult peptide, in which the auxiliary compound is of General Formula III

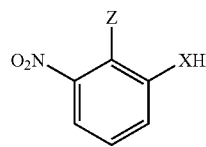

and the auxiliary compound is removed by photolysis following amide bond formation.

7. The method of claim 1, for synthesis of a cyclic peptide, a large peptide, or a difficult peptide containing one or more substituted amide bonds, in which the auxiliary compound is not removed, and the auxiliary compound is of General Formula IV

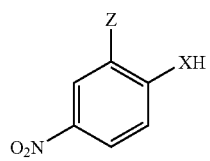

8. A method of
a) synthesis of a linear or cyclic peptide;
b) synthesis of a C-terminal modified peptide; or
c) on-resin cyclization of a peptide molecule,
said method comprising at least the step of linking a cyclic aromatic auxiliary compound of General Formula II to a primary amine nitrogen atom of an amino acid, or of a peptide which is to be cyclized or modified, to form a secondary amine

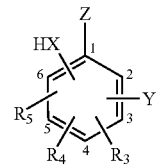

in which
- XH is OH, SH, CH₂OH, or CH₂SH;
- Y is an electron-withdrawing group;
- Z is any group which allows the formation of a covalent carbon-nitrogen bond; and
- $R^3$, $R^4$ and $R^5$ are each independently hydrogen, alkyl, substituted alkyl, aryl, substituted aryl, arylalkyl, substituted arylalkyl, heteroaryl, substituted heteroaryl aryloxy, XH or Y, or a covalent linkage to a solid support; and
- in which $R^3$ and $R^4$, or $R^4$ and $R^5$ can optionally together with the ring form a 5-, 6-, or 7-membered ring, thereby to facilitate conversion of the secondary amine to an amide, activating the carboxylic acid group of the amino acid, or of a peptide which is to be cyclized or modified, and converting the secondary amine to an amide, wherein Y is nitro, ketone, carboxylic ester, amide, nitrile, sulfonamide, sulfoxide, sulfone, sulfonate, fluoride, chloride, bromide or iodide.

9. A method of
a) synthesis of a linear or cyclic peptide;
b) synthesis of a C-terminal modified peptide; or
c) on-resin cyclization of a peptide molecule,
said method comprising at least the step of linking a cyclic aromatic auxiliary compound of General Formula II to a primary amine nitrogen atom of an amino acid, or of a peptide which is to be cyclized or modified, to form a secondary amine,

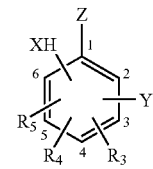

in which
- XH is OH, SH, CH₂OH, or CH₂SH;
- Y is an electron-withdrawing group;
- Z is any group which allows the formation of a covalent carbon-nitrogen bond; and $R^3$, $R^4$ and $R^5$ are each independently hydrogen, alkyl, substituted alkyl, aryl, substituted aryl, arylalkyl, substituted arylalkyl, heteroaryl, substituted heteroaryl aryloxy, XH or Y, or a covalent linkage to a solid support; and
- in which $R^3$ and $R^4$, or $R^4$ and $R^5$ can optionally together with the ring form a 5-, 6-, or 7-membered ring, thereby to facilitate conversion of the secondary amine to an amide, activating the carboxylic acid group of the amino acid, or of a peptide which is to be cyclized or modified, and converting the secondary amine to an amide, wherein Z is an aldehyde, alkylalcohol, alkylhalide, or a ketone, or is a halogenated $C_{1-3}$ alkyl group.

10. The method of claim 9, in which the halogenated $C_{1-3}$ alkyl group is a halogenated methyl group.

11. The method of claim 10, in which the halogen is iodine, bromine or chlorine.

12. A method of
a) synthesis of compound selected from the group consisting of linear and cyclic peptides, large peptides with a native backbone, and "difficult" peptide sequences,
b) backbone linkage for the synthesis of peptides, C-terminal modified peptide, or
c) on-resin cyclization of a peptide molecule,
said method comprising at least the steps of: linking a cyclic aromatic auxiliary compound of General Formula II,

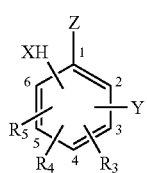

General Formula III,

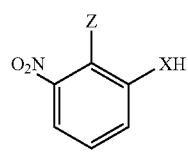

or General Formula IV

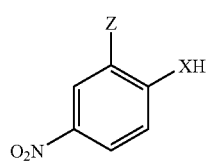

in which
XH is OH, SH, $CH_2OH$, or $CH_2SH$;
Y is an electron-withdrawing group;
Z is any group which allows the formation of a covalent carbon-nitrogen bond; and
$R^3$, $R^4$ and $R^5$ are each independently hydrogen, alkyl, substituted alkyl, aryl, substituted aryl, arylalkyl, substituted arylalkyl, heteroaryl, substituted heteroaryl, alkoxy, aryloxy, XH or Y, or a covalent linkage to a solid support, and
in which $R^3$ and $R^4$, or $R^4$ and $R^5$ can optionally together with the ring form a 5-, 6-, or 7-membered ring,
to a primary amine nitrogen atom of a starting peptide molecule, to form a secondary amine, thereby to facilitate conversion of the secondary amine to an amide, activating the C-terminal carboxylic acid group of the peptide, and converting the secondary amine to an amide;
wherein XH in General Formula II is at position 2, and Y is $NO_2$ at position 6.

13. A method of
a) synthesis of a linear or cyclic peptide;
b) synthesis of a C-terminal modified peptide; or
c) on-resin cyclization of a peptide molecule,
said method comprising at least the step of linking a cyclic aromatic auxiliary compound of General Formula II to a primary amine nitrogen atom of an amino acid, or of a peptide which is to be cyclized or modified, to form a secondary amine,

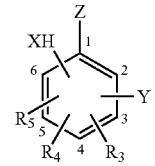

in which
XH is OH, SH, $CH_2OH$, or $CH_2SH$;
Y is an electron-withdrawing group;
Z is any group which allows the formation of a covalent carbon-nitrogen bond; and
$R^3$, $R^4$ and $R^5$ are each independently selected from the group consisting of hydrogen, alkyl, aryl, hydroxy, alkoxy, aryloxy and a covalent linkage to a solid support; and
in which $R^3$ and $R^4$, or $R^4$ and $R^5$ can optionally together with the ring form a 5-, 6-, or 7-membered ring, thereby to facilitate conversion of the secondary amine to an amide, activating the carboxylic acid group of the amino acid, or of a peptide which is to be cyclized or modified, and converting the secondary amine to an amide.

14. A method of synthesis of a cyclic peptide, comprising the steps of
a) synthesizing a linear peptide to be cyclized,
b) linking a cyclic aromatic auxiliary compound of General Formula II

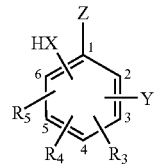

in which
XH is OH, SH, $CH_2OH$, or $CH_2SH$;
Y is an electron-withdrawing group;
Z is any group which allows the formation of a covalent carbon-nitrogen bond; and
$R^3$, $R^4$ and $R^5$ are each independently hydrogen, alkyl, substituted alkyl, aryl, substituted aryl, arylalkyl, substituted arylalkyl, heteroaryl, substituted heteroaryl-aryloxy, XH or Y, or a covalent linkage to a solid support; and
in which $R^3$ and $R^4$, or $R^4$ and $R^5$ can optionally together with the ring form a 5-, 6-, or 7-membered ring,
to a selected primary amine of the linear peptide to form a secondary amine, thereby facilitating conversion of the amine to an amide,
c) activating a selected carboxylic acid to effect cyclization, and where necessary inducing ring contraction, and optionally
d) removing the auxiliary compound after complete N-acylation.

15. The method of claim 14, in which ring contraction is induced by heating or by addition of a metal.

16. The method of claim 14, in which the auxiliary compound is of General Formula III,

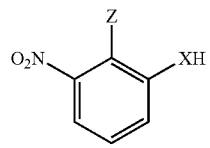

and the auxiliary compound is removed by photolysis.

17. The method of claim 14, in which steps a) to d) are performed on a solid support, and are followed by cleavage of the cyclic product from the solid support.

18. The method of claim 17, in which side-chain protecting groups are removed after cleavage of the cyclic product from the solid support.

19. A method of synthesis of a large peptide with a native peptide backbone, comprising the steps of:
 a) synthesizing a set of peptide fragments to be linked to form a large peptide;
 b) linking a cyclic aromatic auxiliary compound of General Formula II

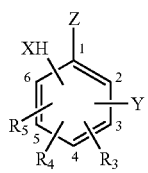

in which
 XH is SH, $CH_2OH$, or $CH_2SH$;
 Y is an electron-withdrawing group selected from the group consisting of nitro, ketone, carboxylic ester, amide, nitrile, sulfonamide, sulfoxide, sulfone, sulfonate, fluoride, chloride, bromide and iodide;
 Z is selected from the group consisting of an alkylalcohol, an alkylhalide, a ketone, and a halogenated $C_{1-3}$ alkyl group, and allows the formation of a covalent carbon-nitrogen bond; and
 $R^3$, $R^4$ and $R^5$ are each independently substituted alkyl, aryl, substituted aryl, arylalkyl, substituted arylalkyl, heteroaryl, substituted heteroaryl, aryloxy, XH or Y, or a covalent linkage to a solid support; and
in which $R^3$ and $R^4$, or $R^4$ and $R^5$ can optionally together with the ring form a 5-, 6-, or 7-membered ring,
 to the primary amine of the first peptide fragment to form a secondary amine, thereby facilitating conversion of the amine to an amide;
 c) activating the C-terminal carboxylic acid of the second peptide fragment;
 d) adding the second peptide fragment to the first peptide fragment and forming a peptide bond between the two fragments; and optionally
 e) removing the auxiliary compound after N-acylation is complete,
wherein steps b) to e) are repeated to add the remaining members of the set of peptide fragments until the large peptide is completed.

20. A method of synthesis of a cyclic peptide, comprising the steps of
 a) synthesizing a linear peptide to be cyclized,
 b) activating a C-terminal carboxylic acid of the linear peptide in the presence of a cyclic aromatic auxiliary compound of General Formula II

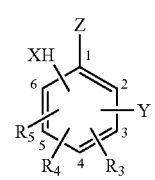

in which
 XH is OH, SH, $CH_2OH$, or $CH_2SH$;
 Y is an electron-withdrawing group;
 Z is any group which allows the formation of a covalent carbon-nitrogen bond; and $R^3$, $R^4$ and $R^5$ are each independently hydrogen, alkyl, substituted alkyl, aryl, substituted aryl, arylalkyl, substituted arylalkyl, heteroaryl, substituted heteroaryl, aryloxy, XH or Y, or a covalent linkage to a solid support; and
in which $R^3$ and $R^4$, or $R^4$ and $R^5$ can optionally together with the ring form a 5-, 6-, or 7-membered ring,
 c) linking the auxiliary compound to a selected primary amine of the linear peptide to form a secondary amine, thereby facilitating conversion of the amine to an amide,
 d) performing cyclization, and where necessary inducing ring contraction, and optionally
 e) removing the auxiliary compound after complete N-acylation;
 III.

21. The method of claim 20, in which the auxiliary compound is of General Formula III,

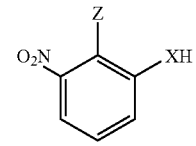

and the method further comprising removing the auxiliary compound by photolysis.

22. A method of synthesis of a difficult peptide sequence, comprising the steps of:
 a) linking a cyclic aromatic auxiliary compound of General Formula II

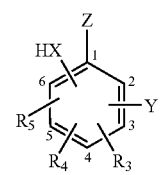

in which
 XH is OH, SH, $CH_2OH$, or $CH_2SH$;
 Y is an electron-withdrawing group;
 Z is any group which allows the formation of a covalent carbon-nitrogen bond; and
 $R^3$, $R^4$ and $R^5$ are each independently hydrogen, alkyl, substituted alkyl, aryl, substituted aryl, arylalkyl, substituted arylalkyl, heteroaryl, substituted heteroaryl, aryloxy, XH or Y, or a covalent linkage to a solid support; and
in which $R^3$ and $R^4$, or $R^4$ and $R^5$ can optionally together with the ring form a 5-, 6-, or 7-membered ring, to one or more α-nitrogen atoms of amino acids in a starting peptide which is linked to a solid support;

b) synthesizing the complete difficult peptide using standard solid phase synthesis methods; and optionally c) when synthesis is complete, removing the auxiliary compound.

23. The method of claim 22, in which the auxiliary compound is of General Formula III,

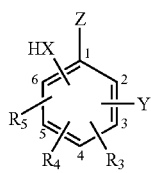

and the auxiliary compound is removed by photolysis.

24. A method of backbone linkage for synthesis of a linear peptide, comprising the steps of:

a) using a cyclic aromatic auxiliary compound of General Formula II

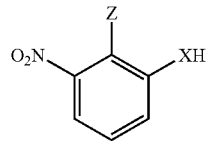

in which

XH is OH, SH, CH$_2$OH, or CH$_2$SH;

Y is an electron-withdrawing group;

Z is any group which allows the formation of a covalent carbon-nitrogen bond; and R$^3$, R$^4$ and R$^5$ are each independently hydrogen, alkyl, substituted alkyl, aryl, substituted aryl, arylalkyl, substituted arylalkyl, heteroaryl, substituted heteroaryl aryloxy, XH or Y, or a covalent linkage to a solid support; and in which R$^3$ and R$^4$, or R$^4$ and R$^5$ can optionally together with the ring form a 5-, 6-, or 7-membered ring, as a linker linking the α-nitrogen of an amino acid residue in the selected peptide to a solid support to form a secondary amine, thereby to facilitate conversion of the amine to an amide;

b) assembling the linear peptide using standard solid phase peptide synthesis methods; and optionally c) removing the side chain protecting group(s); and/or d) cleaving the peptide from the solid support.

25. The method of claim 24, in which the C-terminal amino acid residue of the selected peptide is a modified amino acid in which the carboxyl group is replaced by a functional group.

26. The method of claim 25, in which the functional group is an ester, alkylalcohol, acetal, or amide group.

27. The method of claim 24, in which Y is nitro in position 6, XH is in position 2, and cleavage is performed by photolysis.

28. A method of on-resin cyclization of a linear peptide, comprising the steps of:

a) using a cyclic aromatic auxiliary compound of General Formula II

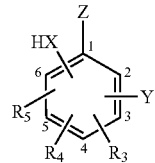

in which

XH is OH, SH, CH$_2$OH, or CH$_2$SH;

Y is an electron-withdrawing group;

Z is any group which allows the formation of a covalent carbon-nitrogen bond; and R$^3$, R$^4$ and R$^5$ are each independently hydrogen, alkyl, substituted alkyl, aryl, substituted aryl, arylalkyl, substituted arylalkyl, heteroaryl, substituted heteroaryl-aryloxy, XH or Y, or a covalent linkage to a solid support; and in which R$^3$ and R$^4$, or R$^4$ and R$^5$ can optionally together with the ring form a 5-, 6-, or 7-membered ring, as a linker linking the α-nitrogen of an amino acid residue in the desired peptide to a solid support to form a secondary amine, thereby to facilitate conversion of the amine to an amide, b) synthesizing a linear peptide on a solid support, using standard solid phase peptide synthesis methods, c) deprotecting the desired amine and carboxylic acid groups;

d) activating the carboxylic acid group to perform cyclization; and optionally e) deprotecting amino acid side chain groups; and/or f) cleaving the cyclic peptide from the solid support.

29. The method of claim 28, in which V is a nitro group in position 6, XH is in position 2, and cleavage is performed by photolysis.

30. A method of a) synthesis of compound selected from the group consisting of linear and cyclic peptides, large peptides with a native backbone, and "difficult" peptide sequences, b) backbone linkage for the synthesis of peptides, C-terminal modified peptide, or c) on-resin cyclization of a peptide molecule, said method comprising at least the steps of: linking a cyclic aromatic auxiliary compound of General Formula II,

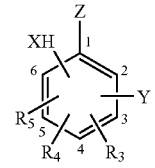

General Formula III,

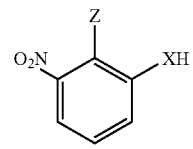

or General Formula IV

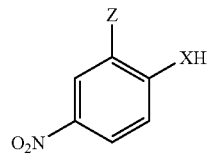

IV in which
XH is OH, SH, CH$_2$OH, or CH$_2$SH;
Y is an electron-withdrawing group;
Z is any group which allows the formation of a covalent carbon-nitrogen bond; and
R$^3$, R$^4$ and R$^5$ are each independently hydrogen, alkyl, substituted alkyl, aryl, substituted aryl, arylalkyl, substituted arylalkyl, heteroaryl, substituted heteroaryl, alkoxy, aryloxy, XH or Y, or a covalent linkage to a solid support, and
in which R$^3$ and R$^4$, or R$^4$ and R$^5$ can optionally together with the ring form a 5-, 6-, or 7-membered ring,
to a primary amine nitrogen atom of a starting peptide molecule, to form a secondary amine, thereby to facilitate conversion of the secondary amine to an amide, activating the C-terminal carboxylic acid group of the peptide, and converting the secondary amine to an amide;
wherein XH in General Formula II is at position 2, and Y is NO$_2$ at position 6, and further wherein R$^3$, R$^4$, and R$^5$ are independently selected from the group consisting of hydrogen, alkyl, aryl, heteroaryl, hydroxy, alkoxy, aryloxy, and a covalent linkage to a solid support.

31. A method of synthesis of a large peptide with a native peptide backbone, comprising the steps of:
a) synthesizing a set of peptide fragments to be linked to form a large peptide;
b) linking a cyclic aromatic auxiliary compound of General Formula II

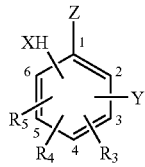

II in which
XH is OH, SH, CH$_2$OH, or CH$_2$SH;
Y is an electron-withdrawing group selected from the group consisting of nitro, ketone, carboxylic ester, amide, nitrile, sulfonamide, sulfoxide, sulfone, sulfonate, fluoride, chloride, bromide and iodide;
Z is selected from the group consisting of an alkylalcohol, an alkylhalide, a ketone, and a halogenated C$_{1-3}$ alkyl group, and allows the formation of a covalent carbon-nitrogen bond; and R$^3$, R$^4$ and R$^5$ are each independently substituted alkyl, aryl, substituted aryl, arylalkyl, substituted arylalkyl, heteroaryl, substituted heteroaryl, aryloxy, XH or Y, or a covalent linkage to a solid support; and
in which R$^3$ and R$^4$, or R$^4$ and R$^5$ can optionally together with the ring form a 5-, 6-, or 7-membered ring,
to the primary amine of the first peptide fragment to form a secondary amine, thereby facilitating conversion of the amine to an amide;
c) activating the C-terminal carboxylic acid of the second peptide fragment;
d) adding the second peptide fragment to the first peptide fragment and forming a peptide bond between the two fragments; and optionally
e) removing the auxiliary compound after N-acylation is complete, wherein steps b) to e) are repeated to add the remaining members of the set of peptide fragments until the large peptide is completed.

32. A method of synthesizing a linear or cyclic peptide, said method comprising at least the steps of:
(i) linking a cyclic aromatic auxiliary compound of the formula:

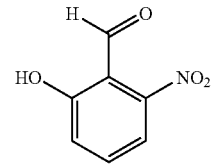

to a primary amine nitrogen atom of an amino acid or of a peptide which is to be cyclized or modified, to form a secondary amine;
(ii) activating the carboxylic acid group of said amino acid or said peptide; and
(iii) converting the resulting secondary amine to an amide.

33. A method of synthesizing a C-terminal modified peptide, said method comprising at least the steps of:
(i) linking a cyclic aromatic auxiliary compound of the formula:

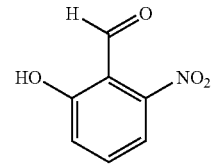

to a primary amine nitrogen atom of an amino acid or of a peptide which is to be cyclized or modified, to form a secondary amine;
(ii) activating the carboxylic acid group of said amino acid or said peptide; and
(iii) converting the resulting secondary amine to an amide.

* * * * *